United States Patent
Sekiguchi et al.

(10) Patent No.: US 10,000,554 B2
(45) Date of Patent: Jun. 19, 2018

(54) MODIFIED LAMININ CONTAINING COLLAGEN BINDING MOLECULE AND USE THEREOF

(71) Applicant: OSAKA UNIVERSITY, Osaka (JP)

(72) Inventors: Kiyotoshi Sekiguchi, Osaka (JP); Shaoliang Li, Osaka (JP); Ryoko Sato, Osaka (JP)

(73) Assignee: OSAKA UNIVERSITY, Osaka (JP)

( * ) Notice: Subject to any disclaimer, the term of this patent is extended or adjusted under 35 U.S.C. 154(b) by 359 days.

(21) Appl. No.: 14/758,061

(22) PCT Filed: Nov. 11, 2013

(86) PCT No.: PCT/JP2013/080405
§ 371 (c)(1),
(2) Date: Jun. 26, 2015

(87) PCT Pub. No.: WO2014/103534
PCT Pub. Date: Jul. 3, 2014

(65) Prior Publication Data
US 2016/0052994 A1  Feb. 25, 2016

(30) Foreign Application Priority Data
Dec. 28, 2012  (JP) .................. 2012-288467

(51) Int. Cl.
| C07K 16/18 | (2006.01) |
| C12N 15/62 | (2006.01) |
| C07K 14/78 | (2006.01) |
| A61L 27/22 | (2006.01) |
| C12N 5/074 | (2010.01) |
| A61K 38/00 | (2006.01) |

(52) U.S. Cl.
CPC ............ *C07K 14/78* (2013.01); *A61L 27/227* (2013.01); *C12N 5/0696* (2013.01); *C07K 2319/00* (2013.01); *C07K 2319/02* (2013.01); *C07K 2319/21* (2013.01); *Y02P 20/582* (2015.11)

(58) Field of Classification Search
None
See application file for complete search history.

(56) References Cited

U.S. PATENT DOCUMENTS

| 6,171,827 B1 * | 1/2001 | Bulleid ............. C07K 14/78 435/252.3 |
| 8,877,493 B2 * | 11/2014 | Sekiguchi ............. C12N 5/0606 435/325 |
| 2009/0022656 A1 * | 1/2009 | Margalit .............. A61K 9/1629 514/1.1 |
| 2009/0215032 A1 * | 8/2009 | White ............. G01N 33/532 435/6.11 |
| 2010/0239633 A1 * | 9/2010 | Strome ............... C07K 16/065 424/423 |
| 2012/0220031 A1 | 8/2012 | Sekiguchi et al. |
| 2013/0116188 A1 * | 5/2013 | Pollock ................ A61K 8/65 514/17.2 |
| 2014/0127806 A1 * | 5/2014 | Sekiguchi ............ C07K 14/78 435/377 |

FOREIGN PATENT DOCUMENTS

| GB | 2 400 852 | 10/2004 |
| JP | 2011-78370 | 4/2011 |
| WO | 2012/137970 | 10/2012 |

OTHER PUBLICATIONS

Mckee et al. (2009) Scaffold-forming and Adhesive Contributions of Synthetic Laminin-binding Proteins to Basement Membrane Assembly, J. Biol. Chem., vol. 284, No. 13, pp. 8984-8994.*
Ido et al. (20070 The Requirement of the Glutamic Acid Residue at the Third Position from the Carboxyl Termini of the Laminin _ Chains in Integrin Binding by Laminins, J. Biol. Chem., vol. 282, No. 15, pp. 11144-11154.*
Extended European Search Report dated Jun. 3, 2016, issued in corresponding European Patent Application No. 13866723.3.
McKee et al., "Scaffold-forming and Adhesive Contributions of Synthetic Laminin-binding Proteins to Basement Membrane Assembly", Journal of Biological Chemistry, 2009, vol. 284, No. 13, pp. 8984-8994.
International Preliminary Report on Patentability dated Jul. 9, 2015 in International Application No. PCT/JP2013/080405.
International Search Report dated Jan. 21, 2014 in International (PCT) Application No. PCT/JP2013/080405.
T. Miyazaki et al., "Recombinant Human Laminin Isoforms can Support the Undifferentiated Growth of Human Embryonic Stem Cells", Biochemical and Biophysical Research Communications, vol. 375, pp. 27-32, 2008.
T. Miyazaki et al., "Laminin E8 Fragments Support Efficient Adhesion and Expansion of Dissociated Human Pluripotent Stem Cells", Nature Communications, DOI: 10.1038/ncomms2231, pp. 1-10, 2012.
M. Hiraoka et al., "Enhanced Survival of Neural Cells Embedded in Hydrogels Composed of Collagen and Laminin-Derived Cell Adhesive Peptide", Bioconjugate Chem., vol. 20, No. 5, pp. 976-983, 2009.
M. Nakamura et al., "Construction of Multi-Functional Extracellular Matrix Proteins that Promote Tube Formation of Endothelial Cells", Biomaterials, vol. 29, No. 20, pp. 2977-2986, 2008.
G. Damodaran et al., "Tethering a Laminin Peptide to a Crosslinked Collagen Scaffold for Biofunctionality", Journal of Biomedical Materials Research Part A, vol. 89A, No. 4, pp. 1001-1010, Jun. 15, 2009.

* cited by examiner

*Primary Examiner* — Manjunath N Rao
*Assistant Examiner* — Samuel W Liu
(74) *Attorney, Agent, or Firm* — Wenderoth, Lind & Ponack, L.L.P.

(57) ABSTRACT

A modified laminin characterized in that a laminin or a heterotrimeric laminin fragment has a collagen binding molecule conjugated to at least one site selected from the α chain N-terminus, the β chain N-terminus and the γ chain N-terminus, and an extracellular-matrix material comprising the modified laminin, and collagen and/or gelatin serve as an alternative to Matrigel and are useful as an extracellular-matrix material for the formation of a safe three-dimensional tissue structure for regenerative medicine in humans.

9 Claims, 13 Drawing Sheets

SEQUENCE LISTING

```
<160> NUMBER OF SEQ ID NOS: 12

<210> SEQ ID NO 1
<211> LENGTH: 1164
<212> TYPE: PRT
<213> ORGANISM: Artificial Sequence
<220> FEATURE:
<223> OTHER INFORMATION: Protein expressed by CBD-LN5E8

<400> SEQUENCE: 1

Met Glu Thr Asp Thr Leu Leu Leu Trp Val Leu Leu Leu Trp Val Pro
1               5                   10                  15

Gly Ser Thr Gly Asp Ala Ala Gln Pro Ala Arg Arg Ala Arg Arg Thr
            20                  25                  30

Lys Leu Val Gln Thr Thr Ser Ser Gly Ser Gly Pro Phe Thr Asp Val
        35                  40                  45

Arg Ala Ala Val Tyr Gln Pro Gln Pro His Pro Gln Pro Pro Pro Tyr
    50                  55                  60

Gly His Cys Val Thr Asp Ser Gly Val Val Tyr Ser Val Gly Met Gln
65                  70                  75                  80

Trp Leu Lys Thr Gln Gly Asn Lys Gln Met Leu Cys Thr Cys Leu Gly
                85                  90                  95

Asn Gly Val Ser Cys Gln Glu Thr Ala Val Thr Gln Thr Tyr Gly Gly
            100                 105                 110

Asn Ser Asn Gly Glu Pro Cys Val Leu Pro Phe Thr Tyr Asn Gly Arg
        115                 120                 125

Thr Phe Tyr Ser Cys Thr Thr Glu Gly Arg Gln Asp Gly His Leu Trp
    130                 135                 140

Cys Ser Thr Thr Ser Asn Tyr Glu Gln Asp Gln Lys Tyr Ser Phe Cys
145                 150                 155                 160

Thr Asp His Thr Val Leu Val Gln Thr Arg Gly Gly Asn Ser Asn Gly
                165                 170                 175

Ala Leu Cys His Phe Pro Phe Leu Tyr Asn Asn His Asn Tyr Thr Asp
            180                 185                 190

Cys Thr Ser Glu Gly Arg Arg Asp Asn Met Lys Trp Cys Gly Thr Thr
        195                 200                 205

Gln Asn Tyr Asp Ala Asp Gln Lys Phe Gly Phe Cys Pro Met Ala Ala
    210                 215                 220

His Glu Glu Ile Cys Thr Thr Asn Glu Gly Val Met Tyr Arg Ile Gly
225                 230                 235                 240

Asp Gln Trp Asp Lys Gln His Asp Met Gly His Met Met Arg Cys Thr
                245                 250                 255

Cys Val Gly Asn Gly Arg Gly Glu Trp Thr Cys Ile Ala Tyr Ser Gln
            260                 265                 270

Leu Arg Asp Gln Cys Ile Val Asp Asp Ile Thr Tyr Asn Val Asn Asp
        275                 280                 285
```

-continued

Thr Phe His Lys Arg His Glu Glu Gly His Met Leu Asn Cys Thr Cys
290                     295                 300

Phe Gly Gln Gly Arg Gly Arg Trp Lys Cys Asp Pro Val Asp Gln Cys
305                 310                 315                 320

Gln Asp Ser Glu Thr Gly Thr Phe Tyr Gln Ile Gly Asp Ser Trp Glu
            325                 330                 335

Lys Tyr Val His Gly Val Arg Tyr Gln Cys Tyr Cys Tyr Gly Arg Gly
            340                 345                 350

Ile Gly Glu Trp His Cys Gln Pro Leu Gln Thr His His His His His
        355                 360                 365

His Asp Ala Ala Glu Asp Ala Ala Gly Gln Ala Leu Gln Gln Ala Asp
370                 375                 380

His Thr Trp Ala Thr Val Val Arg Gln Gly Leu Val Asp Arg Ala Gln
385                 390                 395                 400

Gln Leu Leu Ala Asn Ser Thr Ala Leu Glu Glu Ala Met Leu Gln Glu
                405                 410                 415

Gln Gln Arg Leu Gly Leu Val Trp Ala Ala Leu Gln Gly Ala Arg Thr
            420                 425                 430

Gln Leu Arg Asp Val Arg Ala Lys Lys Asp Gln Leu Glu Ala His Ile
            435                 440                 445

Gln Ala Ala Gln Ala Met Leu Ala Met Asp Thr Asp Glu Thr Ser Lys
450                 455                 460

Lys Ile Ala His Ala Lys Ala Val Ala Ala Glu Ala Gln Asp Thr Ala
465                 470                 475                 480

Thr Arg Val Gln Ser Gln Leu Gln Ala Met Gln Glu Asn Val Glu Arg
                485                 490                 495

Trp Gln Gly Gln Tyr Glu Gly Leu Arg Gly Gln Asp Leu Gly Gln Ala
            500                 505                 510

Val Leu Asp Ala Gly His Ser Val Ser Thr Leu Glu Lys Thr Leu Pro
            515                 520                 525

Gln Leu Leu Ala Lys Leu Ser Ile Leu Glu Asn Arg Gly Val His Asn
530                 535                 540

Ala Ser Leu Ala Leu Ser Ala Ser Ile Gly Arg Val Arg Glu Leu Ile
545                 550                 555                 560

Ala Gln Ala Arg Gly Ala Ala Ser Lys Val Lys Val Pro Met Lys Phe
                565                 570                 575

Asn Gly Arg Ser Gly Val Gln Leu Arg Thr Pro Arg Asp Leu Ala Asp
            580                 585                 590

Leu Ala Ala Tyr Thr Ala Leu Lys Phe Tyr Leu Gln Gly Pro Glu Pro
            595                 600                 605

Glu Pro Gly Gln Gly Thr Glu Asp Arg Phe Val Met Tyr Met Gly Ser
610                 615                 620

Arg Gln Ala Thr Gly Asp Tyr Met Gly Val Ser Leu Arg Asp Lys Lys
625                 630                 635                 640

Val His Trp Val Tyr Gln Leu Gly Glu Ala Gly Pro Ala Val Leu Ser
                645                 650                 655

Ile Asp Glu Asp Ile Gly Glu Gln Phe Ala Ala Val Ser Leu Asp Arg
            660                 665                 670

Thr Leu Gln Phe Gly His Met Ser Val Thr Val Glu Arg Gln Met Ile
            675                 680                 685

Gln Glu Thr Lys Gly Asp Thr Val Ala Pro Gly Ala Glu Gly Leu Leu
690                 695                 700

```
Asn Leu Arg Pro Asp Asp Phe Val Phe Tyr Val Gly Gly Tyr Pro Ser
705                 710                 715                 720

Thr Phe Thr Pro Pro Leu Leu Arg Phe Pro Gly Tyr Arg Gly Cys
            725                 730                 735

Ile Glu Met Asp Thr Leu Asn Glu Glu Val Val Ser Leu Tyr Asn Phe
                740                 745                 750

Glu Arg Thr Phe Gln Leu Asp Thr Ala Val Asp Arg Pro Cys Ala Arg
        755                 760                 765

Ser Lys Ser Thr Gly Asp Pro Trp Leu Thr Asp Gly Ser Tyr Leu Asp
770                 775                 780

Gly Thr Gly Phe Ala Arg Ile Ser Phe Asp Ser Gln Ile Ser Thr Thr
785                 790                 795                 800

Lys Arg Phe Glu Gln Glu Leu Arg Leu Val Ser Tyr Ser Gly Val Leu
                805                 810                 815

Phe Phe Leu Lys Gln Gln Ser Gln Phe Leu Cys Leu Ala Val Gln Glu
                820                 825                 830

Gly Ser Leu Val Leu Leu Tyr Asp Phe Gly Ala Gly Leu Lys Lys Ala
                835                 840                 845

Val Pro Leu Gln Pro Pro Pro Leu Thr Ser Ala Ser Lys Ala Ile
850                 855                 860

Gln Val Phe Leu Leu Gly Gly Ser Arg Lys Arg Val Leu Val Arg Val
865                 870                 875                 880

Glu Arg Ala Thr Val Tyr Ser Val Glu Gln Asp Asn Asp Leu Glu Leu
                885                 890                 895

Ala Asp Ala Tyr Tyr Leu Gly Gly Val Pro Pro Asp Gln Leu Pro Pro
                900                 905                 910

Ser Leu Arg Arg Leu Phe Pro Thr Gly Gly Ser Val Arg Gly Cys Val
            915                 920                 925

Lys Gly Ile Lys Ala Leu Gly Lys Tyr Val Asp Leu Lys Arg Leu Asn
930                 935                 940

Thr Thr Gly Val Ser Ala Gly Cys Thr Ala Asp Leu Leu Val Gly Arg
945                 950                 955                 960

Ala Met Thr Phe His Gly His Gly Phe Leu Arg Leu Ala Leu Ser Asn
                965                 970                 975

Val Ala Pro Leu Thr Gly Asn Val Tyr Ser Gly Phe Gly Phe His Ser
                980                 985                 990

Ala Gln Asp Ser Ala Leu Leu Tyr  Tyr Arg Ala Ser Pro  Asp Gly Leu
                995                 1000                1005

Cys Gln  Val Ser Leu Gln Gln  Gly Arg Val Ser Leu  Gln Leu Leu
    1010                1015                1020

Arg Thr  Glu Val Lys Thr Gln  Ala Gly Phe Ala Asp  Gly Ala Pro
    1025                1030                1035

His Tyr  Val Ala Phe Tyr Ser  Asn Ala Thr Gly Val  Trp Leu Tyr
    1040                1045                1050

Val Asp  Asp Gln Leu Gln Gln  Met Lys Pro His Arg  Gly Pro Pro
    1055                1060                1065

Pro Glu  Leu Gln Pro Gln Pro  Glu Gly Pro Pro Arg  Leu Leu Leu
    1070                1075                1080

Gly Gly  Leu Pro Glu Ser Gly  Thr Ile Tyr Asn Phe  Ser Gly Cys
    1085                1090                1095

Ile Ser  Asn Val Phe Val Gln  Arg Leu Leu Gly Pro  Gln Arg Val
    1100                1105                1110
```

```
Phe Asp Leu Gln Gln Asn Leu Gly Ser Val Asn Val Ser Thr Gly
    1115                1120                1125

Cys Ala Pro Ala Leu Gln Ala Gln Thr Pro Gly Leu Gly Pro Arg
    1130                1135                1140

Gly Leu Gln Ala Thr Ala Arg Lys Ala Ser Arg Arg Ser Arg Gln
    1145                1150                1155

Pro Ala Arg His Pro Ala
    1160

<210> SEQ ID NO 2
<211> LENGTH: 3495
<212> TYPE: DNA
<213> ORGANISM: Artificial Sequence
<220> FEATURE:
<223> OTHER INFORMATION: DNA of protein expressed by CBD-LN5E8

<400> SEQUENCE: 2
```

| | | |
|---|---|---|
| atggagacag acacactcct gctatgggta ctgctgctct gggttccagg ttccactggt | 60 |
| gacgcggccc agccggccag gcgcgcgcgc cgtacgaagc ttgtgcagac cacatcgagc | 120 |
| ggatctggcc ccttcaccga tgttcgtgca gctgtttacc aaccgcagcc tcaccccccag | 180 |
| cctcctccct atggccactg tgtcacagac agtggtgtgg tctactctgt ggggatgcag | 240 |
| tggctgaaga cacaaggaaa taagcaaatg cttttgcacgt gcctgggcaa cggagtcagc | 300 |
| tgccaagaga cagctgtaac ccagacttac ggtggcaact caaatggaga gccatgtgtc | 360 |
| ttaccattca cctacaatgg caggacgttc tactcctgca ccacagaagg gcgacaggac | 420 |
| ggacatcttt ggtgcagcac aacttcgaat tatgagcagg accagaaaata ctcttttctgc | 480 |
| acagaccaca ctgttttggt tcagactcga ggaggaaatt ccaatggtgc cttgtgccac | 540 |
| ttcccccttcc tatacaacaa ccacaattac actgattgca cttctgaggg cagaagagac | 600 |
| aacatgaagt ggtgtgggac cacacagaac tatgatgccg accagaagtt tgggttctgc | 660 |
| cccatggctg cccacgagga aatctgcaca accaatgaag gggtcatgta ccgcattgga | 720 |
| gatcagtggg ataagcagca tgacatgggt cacatgatga ggtgcacgtg tgttgggaat | 780 |
| ggtcgtggag aatggacatg cattgcctac tcgcagcttc gagatcagtg cattgttgat | 840 |
| gacatcactt acaatgtgaa cgacacattc cacaagcgtc atgaagaggg cacatgctgg | 900 |
| aactgtacat gcttcggtca gggtcggggc aggtggaagt gtgatcccgt cgaccaatgc | 960 |
| caggattcag agactgggac gttttatcaa attggagatt catgggagaa gtatgtgcat | 1020 |
| ggtgtcagat accagtgcta ctgctatggc cgtggcattg ggagtggca ttgccaacct | 1080 |
| ttacagaccc atcatcatca tcatcatgat gctgccgagg atgctgctgg ccaggccctg | 1140 |
| cagcaggcgg accacgtgg gcgacggtg gtgcggcagg gcctggtgga ccgagcccag | 1200 |
| cagctcctgg ccaacagcac tgcactagaa gaggccatgc tccaggaaca gcagaggctg | 1260 |
| ggccttgtgt gggctgccct ccagggtgcc aggacccagc tccgagatgt ccgggccaag | 1320 |
| aaggaccagc tggaggcgca catccaggcg gcgcaggcca tgcttgccat ggacacagac | 1380 |
| gagacaagca agaagatcgc acatgccaag gctgtggctg ctgaagccca ggacaccgcc | 1440 |
| acccgtgtgc agtcccagct gcaggccatg caggagaatg tggagcggtg cagggccag | 1500 |
| tacgagggcc tgcggggcca ggacctgggc caggcagtgc ttgacgcagg ccactcagtg | 1560 |
| tccaccctgg agaagacgct gccccagctg ctggccaagc tgagcatcct ggagaaccgt | 1620 |
| ggggtgcaca cgccagcct ggccctgtcc gccagcattg ccgcgtgcg agagctcatt | 1680 |
| gcccaggccc gggggggctgc cagtaaggtc aaggtgccca tgaagttcaa cggcgctca | 1740 |

-continued

| | |
|---|---|
| ggggtgcagc tgcgcacccc acgggatctt gccgaccttg ctgcctacac tgccctcaag | 1800 |
| ttctacctgc agggcccaga gcctgagcct gggcaggta ccgaggatcg ctttgtgatg | 1860 |
| tacatgggca gccgccaggc cactggggac tacatgggtg tgtctctgcg tgacaagaag | 1920 |
| gtgcactggg tgtatcagct gggtgaggcg ggccctgcag tcctaagcat cgatgaggac | 1980 |
| attggggagc agttcgcagc tgtcagcctg acaggactc tccagtttgg ccacatgtcc | 2040 |
| gtcacagtgg agagacagat gatccaggaa accaagggtg acacggtggc ccctggggca | 2100 |
| gaggggctgc tcaacctgcg gccagacgac ttcgtcttct acgtcggggg gtaccccagt | 2160 |
| accttcacgc cccctcccct gcttcgcttc cccggctacc ggggctgcat cgagatggac | 2220 |
| acgctgaatg aggaggtggt cagcctctac aacttcgaga ggaccttcca gctggacacg | 2280 |
| gctgtggaca ggccttgtgc ccgctccaag tcgaccgggg accgtggct cacggacggc | 2340 |
| tcctacctgg acggcaccgg cttcgcccgc atcagcttcg acagtcagat cagcaccacc | 2400 |
| aagcgcttcg agcaggagct gcggctcgtg tcctacagcg gggtgctctt cttcctgaag | 2460 |
| cagcagagcc agttcctgtg cttggccgtg caagaaggca gcctcgtgct gttgtatgac | 2520 |
| tttggggctg gcctgaaaaa ggccgtccca ctgcagcccc caccgccct gacctcggcc | 2580 |
| agcaaggcga tccaggtgtt cctgctgggg ggcagccgca gcgtgtgct ggtgcgtgtg | 2640 |
| gagcgggcca cggtgtacag cgtggagcag gacaatgatc tggagctggc cgacgcctac | 2700 |
| tacctggggg gcgtgccgcc cgaccagctg cccccgagcc tgcgacggct cttccccacc | 2760 |
| ggaggctcag tccgtggctg cgtcaaaggc atcaaggccc tgggcaagta tgtggacctc | 2820 |
| aagcggctga acacgacagg cgtgagcgcc ggctgcaccg ccgacctgct ggtggggcgc | 2880 |
| gccatgactt tccatggcca cggcttcctt cgcctggcgc tctcgaacgt ggaccgctc | 2940 |
| actggcaacg tctactccgg cttcggcttc acagcgccc aggacagtgc cctgctctac | 3000 |
| taccgggcgt ccccggatgg gctatgccag gtgtccctgc agcagggccg tgtgagccta | 3060 |
| cagctcctga ggactgaagt gaaaactcaa gcgggcttcg ccgatggtgc cccccattac | 3120 |
| gtcgccttct acagcaatgc cacgggagtc tggctgtatg tcgatgacca gctccagcag | 3180 |
| atgaagcccc accggggacc accccccgag ctccagccgc agcctgaggg gccccccgagg | 3240 |
| ctcctcctgg gaggcctgcc tgagtctggc accatttaca acttcagtgg ctgcatcagc | 3300 |
| aacgtcttcg tgcagcggct cctgggccca cagcgcgtat ttgatctgca gcagaacctg | 3360 |
| ggcagcgtca atgtgagcac gggctgtgca cccgccctgc aagcccagac ccgggcctg | 3420 |
| gggcctagag gactgcaggc caccgcccgg aaggcctccc gccgcagccg tcagcccgcc | 3480 |
| cggcatcctg cctag | 3495 |

<210> SEQ ID NO 3
<211> LENGTH: 599
<212> TYPE: PRT
<213> ORGANISM: Artificial Sequence
<220> FEATURE:
<223> OTHER INFORMATION: Protein expressed by CBD-LN1E8

<400> SEQUENCE: 3

Met Glu Thr Asp Thr Leu Leu Leu Trp Val Leu Leu Leu Trp Val Pro
1               5                   10                  15

Gly Ser Thr Gly Asp Ala Ala Gln Pro Ala Arg Arg Ala Arg Arg Thr
            20                  25                  30

Lys Leu Val Gln Thr Thr Ser Ser Gly Ser Gly Pro Phe Thr Asp Val
        35                  40                  45

-continued

```
Arg Ala Val Tyr Gln Pro Gln Pro His Pro Gln Pro Pro Tyr
    50              55                  60
Gly His Cys Val Thr Asp Ser Gly Val Val Tyr Ser Val Gly Met Gln
65                  70                  75                  80
Trp Leu Lys Thr Gln Gly Asn Lys Gln Met Leu Cys Thr Cys Leu Gly
                85                  90                  95
Asn Gly Val Ser Cys Gln Glu Thr Ala Val Thr Gln Thr Tyr Gly Gly
            100                 105                 110
Asn Ser Asn Gly Glu Pro Cys Val Leu Pro Phe Thr Tyr Asn Gly Arg
            115                 120                 125
Thr Phe Tyr Ser Cys Thr Thr Glu Gly Arg Gln Asp Gly His Leu Trp
    130                 135                 140
Cys Ser Thr Thr Ser Asn Tyr Glu Gln Asp Gln Lys Tyr Ser Phe Cys
145                 150                 155                 160
Thr Asp His Thr Val Leu Val Gln Thr Arg Gly Gly Asn Ser Asn Gly
                165                 170                 175
Ala Leu Cys His Phe Pro Phe Leu Tyr Asn Asn His Asn Tyr Thr Asp
            180                 185                 190
Cys Thr Ser Glu Gly Arg Arg Asp Asn Met Lys Trp Cys Gly Thr Thr
            195                 200                 205
Gln Asn Tyr Asp Ala Asp Gln Lys Phe Gly Phe Cys Pro Met Ala Ala
    210                 215                 220
His Glu Glu Ile Cys Thr Thr Asn Glu Gly Val Met Tyr Arg Ile Gly
225                 230                 235                 240
Asp Gln Trp Asp Lys Gln His Asp Met Gly His Met Met Arg Cys Thr
                245                 250                 255
Cys Val Gly Asn Gly Arg Gly Glu Trp Thr Cys Ile Ala Tyr Ser Gln
            260                 265                 270
Leu Arg Asp Gln Cys Ile Val Asp Asp Ile Thr Tyr Asn Val Asn Asp
            275                 280                 285
Thr Phe His Lys Arg His Glu Glu Gly His Met Leu Asn Cys Thr Cys
    290                 295                 300
Phe Gly Gln Gly Arg Gly Arg Trp Lys Cys Asp Pro Val Asp Gln Cys
305                 310                 315                 320
Gln Asp Ser Glu Thr Gly Thr Phe Tyr Gln Ile Gly Asp Ser Trp Glu
                325                 330                 335
Lys Tyr Val His Gly Val Arg Tyr Gln Cys Tyr Cys Tyr Gly Arg Gly
            340                 345                 350
Ile Gly Glu Trp His Cys Gln Pro Leu Gln Thr Tyr Pro Tyr Asp Val
            355                 360                 365
Pro Asp Tyr Ala Asp Leu Gln His Ser Ala Ala Asp Ile Ala Arg Ala
    370                 375                 380
Glu Met Leu Leu Glu Glu Ala Lys Arg Ala Ser Lys Ser Ala Thr Asp
385                 390                 395                 400
Val Lys Val Thr Ala Asp Met Val Lys Glu Ala Leu Glu Glu Ala Glu
                405                 410                 415
Lys Ala Gln Val Ala Ala Glu Lys Ala Ile Lys Gln Ala Asp Glu Asp
            420                 425                 430
Ile Gln Gly Thr Gln Asn Leu Leu Thr Ser Ile Glu Ser Glu Thr Ala
            435                 440                 445
Ala Ser Glu Glu Thr Leu Phe Asn Ala Ser Gln Arg Ile Ser Glu Leu
    450                 455                 460
```

Glu Arg Asn Val Glu Glu Leu Lys Arg Lys Ala Ala Gln Asn Ser Gly
465                 470                 475                 480

Glu Ala Glu Tyr Ile Glu Lys Val Val Tyr Thr Val Lys Gln Ser Ala
            485                 490                 495

Glu Asp Val Lys Lys Thr Leu Asp Gly Glu Leu Asp Glu Lys Tyr Lys
        500                 505                 510

Lys Val Glu Asn Leu Ile Ala Lys Lys Thr Glu Glu Ser Ala Asp Ala
        515                 520                 525

Arg Arg Lys Ala Glu Met Leu Gln Asn Glu Ala Lys Thr Leu Leu Ala
530                 535                 540

Gln Ala Asn Ser Lys Leu Gln Leu Leu Lys Asp Leu Glu Arg Lys Tyr
545                 550                 555                 560

Glu Asp Asn Gln Arg Tyr Leu Glu Asp Lys Ala Gln Glu Leu Ala Arg
                565                 570                 575

Leu Glu Gly Glu Val Arg Ser Leu Leu Lys Asp Ile Ser Gln Lys Val
            580                 585                 590

Ala Val Tyr Ser Thr Cys Leu
            595

<210> SEQ ID NO 4
<211> LENGTH: 1800
<212> TYPE: DNA
<213> ORGANISM: Artificial Sequence
<220> FEATURE:
<223> OTHER INFORMATION: DNA of protein expressed by CBD-LN1E8

<400> SEQUENCE: 4
atggagacag acacactcct gctatgggta ctgctgctct gggttccagg ttccactggt      60
gacgcggccc agccggccag gcgcgcgcgc cgtacgaagc ttgtgcagac acatcgagc     120 ggatctggcc ccttcaccga tgttcgtgca gctgtttacc aaccgcagcc tcaccccag     180 cctcctccct atggccactg tgtcacagac agtggtgtgg tctactctgt ggggatgcag     240
tggctgaaga cacaaggaaa taagcaaatg ctttgcacgt gcctgggcaa cggagtcagc     300
tgccaagaga cagctgtaac ccagacttac ggtggcaact caaatggaga gccatgtgtc     360
ttaccattca cctacaatgg caggacgttc tactcctgca ccacagaagg gcgacaggac     420
ggacatcttt ggtgcagcac aacttcgaat tatgagcagg accagaaata ctctttctgc     480
acagaccaca ctgttttggt tcagactcga ggaggaaatt ccaatggtgc cttgtgccac     540
ttccccttcc tatacaacaa ccacaattac actgattgca cttctgaggg cagaagagac     600
aacatgaagt ggtgtgggac cacacagaac tatgatgccg accagaagtt tgggttctgc     660
cccatggctg cccacgagga aatctgcaca accaatgaag gggtcatgta ccgcattgga     720
gatcagtggg ataagcagca tgacatgggt cacatgatga ggtgcacgtg tgttgggaat     780
ggtcgtggag aatggacatg cattgcctac tcgcagcttc gagatcagtg cattgttgat     840
gacatcactt acaatgtgaa cgacacattc acaagcgtc atgaagaggg gcacatgctg     900
aactgtacat gcttcggtca gggtcggggc aggtggaagt gtgatcccgt cgaccaatgc     960
caggattcag agactgggac gttttatcaa attggagatt catgggagaa gtatgtgcat    1020
ggtgtcagat accagtgcta ctgctatggc cgtggcattg gggagtggca ttgccaacct    1080
ttacagacct atccatatga tgtgccagat tatgcagatc ttcagcatag tgctgctgac    1140
attgccagag ctgagatgtt gttagaagaa gctaaagag caagcaaaag tgcaacagat    1200
gttaaagtca ctgcagatat ggtaaaggaa gctctggaag aagcagaaaa ggcccaggtc    1260

-continued

```
gcagcagaga aggcaattaa acaagcagat gaagacattc aaggaaccca gaacctgtta   1320
acttcgattg agtctgaaac agcagcttct gaggaaacct tgttcaacgc gtcccagcgc   1380
atcagcgagt tagagaggaa tgtggaagaa cttaagcgga aagctgccca aaactccggg   1440
gaggcagaat atattgaaaa agtagtatat actgtgaagc aaagtgcaga agatgttaag   1500
aagactttag atggtgaact tgatgaaaag tataaaaaag tagaaaattt aattgccaaa   1560
aaaactgaag agtcagctga tgccagaagg aaagccgaaa tgctacaaaa tgaagcaaaa   1620
actcttttag ctcaagcaaa tagcaagctg caactgctca agatttaga aagaaaatat    1680 gaagacaatc aaagatactt agaagataaa gctcaagaat tagcaagact ggaaggagaa   1740
gtccgttcac tcctaaagga tataagccag aaagttgctg tgtatagcac atgcttgtaa   1800
```

<210> SEQ ID NO 5
<211> LENGTH: 618
<212> TYPE: PRT
<213> ORGANISM: Artificial Sequence
<220> FEATURE:
<223> OTHER INFORMATION: Protein expressed by CBD-LN1E8

<400> SEQUENCE: 5

```
Met Glu Thr Asp Thr Leu Leu Leu Trp Val Leu Leu Leu Trp Val Pro
 1               5                  10                  15

Gly Ser Thr Gly Asp Ala Ala Gln Pro Ala Arg Arg Ala Arg Arg Thr
            20                  25                  30

Lys Leu Val Gln Thr Thr Ser Ser Gly Ser Gly Pro Phe Thr Asp Val
        35                  40                  45

Arg Ala Val Tyr Gln Pro Gln Pro His Pro Gln Pro Pro Pro Tyr
    50                  55                  60

Gly His Cys Val Thr Asp Ser Gly Val Val Tyr Ser Val Gly Met Gln
65                  70                  75                  80

Trp Leu Lys Thr Gln Gly Asn Lys Gln Met Leu Cys Thr Cys Leu Gly
                85                  90                  95

Asn Gly Val Ser Cys Gln Glu Thr Ala Val Thr Gln Thr Tyr Gly Gly
            100                 105                 110

Asn Ser Asn Gly Glu Pro Cys Val Leu Pro Phe Thr Tyr Asn Gly Arg
        115                 120                 125

Thr Phe Tyr Ser Cys Thr Thr Glu Gly Arg Gln Asp Gly His Leu Trp
    130                 135                 140

Cys Ser Thr Thr Ser Asn Tyr Glu Gln Asp Gln Lys Tyr Ser Phe Cys
145                 150                 155                 160

Thr Asp His Thr Val Leu Val Gln Thr Arg Gly Gly Asn Ser Asn Gly
                165                 170                 175

Ala Leu Cys His Phe Pro Phe Leu Tyr Asn Asn His Asn Tyr Thr Asp
            180                 185                 190

Cys Thr Ser Glu Gly Arg Arg Asp Asn Met Lys Trp Cys Gly Thr Thr
        195                 200                 205

Gln Asn Tyr Asp Ala Asp Gln Lys Phe Gly Phe Cys Pro Met Ala Ala
    210                 215                 220

His Glu Glu Ile Cys Thr Thr Asn Glu Gly Val Met Tyr Arg Ile Gly
225                 230                 235                 240

Asp Gln Trp Asp Lys Gln His Asp Met Gly His Met Met Arg Cys Thr
                245                 250                 255

Cys Val Gly Asn Gly Arg Gly Glu Trp Thr Cys Ile Ala Tyr Ser Gln
            260                 265                 270
```

| | | | | | | | | | | | |
|---|---|---|---|---|---|---|---|---|---|---|---|
|Leu|Arg|Asp|Gln|Cys|Ile|Val|Asp|Ile|Thr|Tyr|Asn|Val|Asn|Asp|
| | |275| | | |280| | | |285| |

Thr Phe His Lys Arg His Glu Glu Gly His Met Leu Asn Cys Thr Cys
    290                 295                 300

Phe Gly Gln Gly Arg Gly Arg Trp Lys Cys Asp Pro Val Asp Gln Cys
305                 310                 315                 320

Gln Asp Ser Glu Thr Gly Thr Phe Tyr Gln Ile Gly Asp Ser Trp Glu
                325                 330                 335

Lys Tyr Val His Gly Val Arg Tyr Gln Cys Tyr Cys Tyr Gly Arg Gly
            340                 345                 350

Ile Gly Glu Trp His Cys Gln Pro Leu Gln Thr Asp Tyr Lys Asp Asp
            355                 360                 365

Asp Asp Lys Asp Asn Asp Ile Leu Asn Asn Leu Lys Asp Phe Asp Arg
    370                 375                 380

Arg Val Asn Asp Asn Lys Thr Ala Ala Glu Ala Leu Arg Lys Ile
385                 390                 395                 400

Pro Ala Ile Asn Gln Thr Ile Thr Glu Ala Asn Glu Lys Thr Arg Glu
                405                 410                 415

Ala Gln Gln Ala Leu Gly Ser Ala Ala Ala Asp Ala Thr Glu Ala Lys
            420                 425                 430

Asn Lys Ala His Glu Ala Glu Arg Ile Ala Ser Ala Val Gln Lys Asn
    435                 440                 445

Ala Thr Ser Thr Lys Ala Glu Ala Glu Arg Thr Phe Ala Glu Val Thr
    450                 455                 460

Asp Leu Asp Asn Glu Val Asn Asn Met Leu Lys Gln Leu Gln Glu Ala
465                 470                 475                 480

Glu Lys Glu Leu Lys Arg Lys Gln Asp Asp Ala Asp Gln Asp Met Met
                485                 490                 495

Met Ala Gly Met Ala Ser Gln Ala Ala Gln Glu Ala Glu Ile Asn Ala
            500                 505                 510

Arg Lys Ala Lys Asn Ser Val Thr Ser Leu Leu Ser Ile Ile Asn Asp
    515                 520                 525

Leu Leu Glu Gln Leu Gly Gln Leu Asp Thr Val Asp Leu Asn Lys Leu
    530                 535                 540

Asn Glu Ile Glu Gly Thr Leu Asn Lys Ala Lys Asp Glu Met Lys Val
545                 550                 555                 560

Ser Asp Leu Asp Arg Lys Val Ser Asp Leu Glu Asn Glu Ala Lys Lys
                565                 570                 575

Gln Glu Ala Ala Ile Met Asp Tyr Asn Arg Asp Ile Glu Glu Ile Met
            580                 585                 590

Lys Asp Ile Arg Asn Leu Glu Asp Ile Arg Lys Thr Leu Pro Ser Gly
    595                 600                 605

Cys Phe Asn Thr Pro Ser Ile Glu Lys Pro
    610                 615

<210> SEQ ID NO 6
<211> LENGTH: 1857
<212> TYPE: DNA
<213> ORGANISM: Artificial Sequence
<220> FEATURE:
<223> OTHER INFORMATION: DNA of protein expressed by CBD-LN1E8

<400> SEQUENCE: 6
atggagacag acacactcct gctatgggta ctgctgctct gggttccagg ttccactggt    60
gacgcggccc agccggccag gcgcgcgcgc cgtacgaagc ttgtgcagac cacatcgagc   120

```
ggatctggcc ccttcaccga tgttcgtgca gctgtttacc aaccgcagcc tcaccccag     180 cctcctccct atggccactg tgtcacagac agtggtgtgg tctactctgt ggggatgcag    240
tggctgaaga cacaaggaaa taagcaaatg ctttgcacgt gcctgggcaa cggagtcagc    300
tgccaagaga cagctgtaac ccagacttac ggtggcaact caaatggaga gccatgtgtc    360
ttaccattca cctacaatgg caggacgttc tactcctgca ccacagaagg gcgacaggac    420
ggacatcttt ggtgcagcac aacttcgaat tatgagcagg accagaaata ctctttctgc    480
acagaccaca ctgttttggt tcagactcga ggaggaaatt ccaatggtgc cttgtgccac    540
ttccccttcc tatacaacaa ccacaattac actgattgca cttctgaggg cagaagagac    600
aacatgaagt ggtgtgggac cacacagaac tatgatgccg accagaagtt tgggttctgc    660
cccatggctg cccacgagga aatctgcaca accaatgaag gggtcatgta ccgcattgga    720
gatcagtggg ataagcagca tgacatgggt cacatgatga ggtgcacgtg tgttgggaat    780
ggtcgtggag aatggacatg cattgcctac tcgcagcttc gagatcagtg cattgttgat    840
gacatcactt acaatgtgaa cgacacattc cacaagcgtc atgaagaggg gcacatgctg    900
aactgtacat gcttcggtca gggtcggggc aggtggaagt gtgatcccgt cgaccaatgc    960
caggattcag agactgggac gttttatcaa attggagatt catgggagaa gtatgtgcat   1020
ggtgtcagat accagtgcta ctgctatggc cgtggcattg gggagtggca ttgccaacct   1080
ttacagaccg attacaagga tgatgatgat aaggataatg acattctcaa caacctgaaa   1140
gattttgata ggcgcgtgaa cgataacaag acggccgcag aggaggcact aaggaagatt   1200
cctgccatca accagaccat cactgaagcc aatgaaaaga ccagagaagc ccagcaggcc   1260
ctgggcagtg ctgcggcgga tgccacagag gccaagaaca aggcccatga ggcggagagg   1320
atcgcaagcg ctgtccaaaa gaatgccacc agcaccaagg cagaagctga agaacttttt   1380
gcagaagtta cagatctgga taatgaggtg aacaatatgt tgaagcaact gcaggaagca   1440
gaaaaagagc taaagagaaa acaagatgac gctgaccagg acatgatgat ggcagggatg   1500
gcttcacagg ctgctcaaga agccgagatc aatgccagaa agccaaaaaa ctctgttact   1560
agcctcctca gcattattaa tgacctcttg gagcagctgg ggcagctgga tacagtggac   1620
ctgaataagc taaacgagat tgaaggcacc ctaaacaaag ccaaagatga aatgaaggtc   1680
agcgatcttg ataggaaagt gtctgacctg gagaatgaag ccaagaagca ggaggctgcc   1740
atcatggact ataaccgaga tatcgaggag atcatgaagg acattcgcaa tctggaggac   1800
atcaggaaga ccttaccatc tggctgcttc aacaccccgt ccattgaaaa gccctag      1857
```

<210> SEQ ID NO 7
<211> LENGTH: 34
<212> TYPE: DNA
<213> ORGANISM: Artificial Sequence
<220> FEATURE:
<223> OTHER INFORMATION: Synthetic Primer

<400> SEQUENCE: 7
atgatgatgg gcgcgccaag cttatcgata ccgt       34

<210> SEQ ID NO 8
<211> LENGTH: 25
<212> TYPE: DNA
<213> ORGANISM: Artificial Sequence
<220> FEATURE:
<223> OTHER INFORMATION: Synthetic Primer

```
<400> SEQUENCE: 8
catcatcatg atatcgaatt cctgc                                          25

<210> SEQ ID NO 9
<211> LENGTH: 34
<212> TYPE: DNA
<213> ORGANISM: Artificial Sequence
<220> FEATURE:
<223> OTHER INFORMATION: Synthetic Primer

<400> SEQUENCE: 9
gaggtctata taagcagagc tctctggcta acta                                34

<210> SEQ ID NO 10
<211> LENGTH: 35
<212> TYPE: DNA
<213> ORGANISM: Artificial Sequence
<220> FEATURE:
<223> OTHER INFORMATION: Synthetic Primer

<400> SEQUENCE: 10
cattggcttc atcatgatga tgatgatgat gaagc                               35

<210> SEQ ID NO 11
<211> LENGTH: 609
<212> TYPE: PRT
<213> ORGANISM: Artificial Sequence
<220> FEATURE:
<223> OTHER INFORMATION: Protein expressed by CBD-LN2E8

<400> SEQUENCE: 11
```

Met Glu Thr Asp Thr Leu Leu Leu Trp Val Leu Leu Leu Trp Val Pro
1               5                   10                  15

Gly Ser Thr Gly Asp Ala Ala Gln Pro Ala Arg Arg Ala Arg Arg Thr
            20                  25                  30

Lys Leu Val Gln Thr Thr Ser Ser Gly Ser Gly Pro Phe Thr Asp Val
        35                  40                  45

Arg Ala Ala Val Tyr Gln Pro Gln Pro His Pro Gln Pro Pro Pro Tyr
    50                  55                  60

Gly His Cys Val Thr Asp Ser Gly Val Val Tyr Ser Val Gly Met Gln
65                  70                  75                  80

Trp Leu Lys Thr Gln Gly Asn Lys Gln Met Leu Cys Thr Cys Leu Gly
                85                  90                  95

Asn Gly Val Ser Cys Gln Glu Thr Ala Val Thr Gln Thr Tyr Gly Gly
            100                 105                 110

Asn Ser Asn Gly Glu Pro Cys Val Leu Pro Phe Thr Tyr Asn Gly Arg
        115                 120                 125

Thr Phe Tyr Ser Cys Thr Thr Glu Gly Arg Gln Asp Gly His Leu Trp
    130                 135                 140

Cys Ser Thr Thr Ser Asn Tyr Glu Gln Asp Gln Lys Tyr Ser Phe Cys
145                 150                 155                 160

Thr Asp His Thr Val Leu Val Gln Thr Arg Gly Gly Asn Ser Asn Gly
                165                 170                 175

Ala Leu Cys His Phe Pro Phe Leu Tyr Asn Asn His Asn Tyr Thr Asp
            180                 185                 190

Cys Thr Ser Glu Gly Arg Arg Asp Asn Met Lys Trp Cys Gly Thr Thr
        195                 200                 205

Gln Asn Tyr Asp Ala Asp Gln Lys Phe Gly Phe Cys Pro Met Ala Ala
    210                 215                 220

-continued

His Glu Glu Ile Cys Thr Thr Asn Glu Gly Val Met Tyr Arg Ile Gly
225                 230                 235                 240

Asp Gln Trp Asp Lys Gln His Asp Met Gly His Met Met Arg Cys Thr
            245                 250                 255

Cys Val Gly Asn Gly Arg Gly Glu Trp Thr Cys Ile Ala Tyr Ser Gln
        260                 265                 270

Leu Arg Asp Gln Cys Ile Val Asp Asp Ile Thr Tyr Asn Val Asn Asp
    275                 280                 285

Thr Phe His Lys Arg His Glu Gly His Met Leu Asn Cys Thr Cys
    290                 295                 300

Phe Gly Gln Gly Arg Gly Arg Trp Lys Cys Asp Pro Val Asp Gln Cys
305                 310                 315                 320

Gln Asp Ser Glu Thr Gly Thr Phe Tyr Gln Ile Gly Asp Ser Trp Glu
            325                 330                 335

Lys Tyr Val His Gly Val Arg Tyr Gln Cys Tyr Cys Tyr Gly Arg Gly
        340                 345                 350

Ile Gly Glu Trp His Cys Gln Pro Leu Gln Thr Tyr Pro Tyr Asp Val
    355                 360                 365

Pro Asp Tyr Ala Asp Tyr Pro Tyr Asp Val Pro Asp Tyr Ala Asp Leu
370                 375                 380

Ala Arg Thr Val Gly Asp Val Arg Ala Glu Gln Leu Leu Gln Asp
385                 390                 395                 400

Ala Arg Arg Ala Arg Ser Trp Ala Glu Asp Lys Gln Lys Ala Glu
            405                 410                 415

Thr Val Gln Ala Ala Leu Glu Glu Ala Gln Arg Ala Gln Gly Ile Ala
        420                 425                 430

Gln Gly Ala Ile Arg Gly Ala Val Ala Asp Thr Arg Asp Thr Glu Gln
    435                 440                 445

Thr Leu Tyr Gln Val Gln Glu Arg Met Ala Gly Ala Glu Arg Ala Leu
450                 455                 460

Ser Ser Ala Gly Glu Arg Ala Arg Gln Leu Asp Ala Leu Leu Glu Ala
465                 470                 475                 480

Leu Lys Leu Lys Arg Ala Gly Asn Ser Leu Ala Ala Ser Thr Ala Glu
            485                 490                 495

Glu Thr Ala Gly Ser Ala Gln Gly Arg Ala Gln Glu Ala Glu Gln Leu
        500                 505                 510

Leu Arg Gly Pro Leu Gly Asp Gln Tyr Gln Thr Val Lys Ala Leu Ala
    515                 520                 525

Glu Arg Lys Ala Gln Gly Val Leu Ala Ala Gln Ala Arg Ala Glu Gln
530                 535                 540

Leu Arg Asp Glu Ala Arg Asp Leu Leu Gln Ala Ala Gln Asp Lys Leu
545                 550                 555                 560

Gln Arg Leu Gln Glu Leu Glu Gly Thr Tyr Glu Glu Asn Glu Arg Ala
            565                 570                 575

Leu Glu Ser Lys Ala Ala Gln Leu Asp Gly Leu Glu Ala Arg Met Arg
        580                 585                 590

Ser Val Leu Gln Ala Ile Asn Leu Gln Val Gln Ile Tyr Asn Thr Cys
    595                 600                 605

Gln

<210> SEQ ID NO 12
<211> LENGTH: 1830
<212> TYPE: DNA
<213> ORGANISM: Artificial Sequence
<220> FEATURE:
<223> OTHER INFORMATION: DNA of protein expressed by CBD-LN2E8

<400> SEQUENCE: 12

```
atggagacag acacactcct gctatgggta ctgctgctct gggttccagg ttccactggt      60
gacgcggccc agccggccag gcgcgcgcgc cgtacgaagc ttgtgcagac cacatcgagc     120
ggatctggcc ccttcaccga tgttcgtgca gctgtttacc aaccgcagcc tcaccccag     180
cctcctccct atggccactg tgtcacagac agtggtgtgg tctactctgt ggggatgcag     240
tggctgaaga cacaaggaaa taagcaaatg ctttgcacgt gcctgggcaa cggagtcagc     300
tgccaagaga cagctgtaac ccagacttac ggtggcaact caaatggaga gccatgtgtc     360
ttaccattca cctacaatgg caggacgttc tactcctgca ccacagaagg gcgacaggac     420
ggacatcttt ggtgcagcac aacttcgaat tatgagcagg accagaaata ctctttctgc     480
acagaccaca ctgttttggt tcagactcga ggaggaaatt ccaatggtgc cttgtgccac     540
ttccccttcc tatacaacaa ccacaattac actgattgca cttctgaggg cagaagagac     600
aacatgaagt ggtgtgggac cacacagaac tatgatgccg accagaagtt tgggttctgc     660
cccatggctg cccacgagga aatctgcaca accaatgaag gggtcatgta ccgcattgga     720
gatcagtggg ataagcagca tgacatgggt cacatgatga ggtgcacgtg tgttgggaat     780
ggtcgtggag aatggacatg cattgcctac tcgcagcttc gagatcagtg cattgttgat     840
gacatcactt acaatgtgaa cgacacattc cacaagcgtc atgaagaggg gcacatgctg     900
aactgtacat gcttcggtca gggtcggggc aggtggaagt gtgatcccgt cgaccaatgc     960
caggattcag agactgggac gttttatcaa attggagatt catgggagaa gtatgtgcat    1020
ggtgtcagat accagtgcta ctgctatggc cgtggcattg gggagtggca ttgccaacct    1080
ttacagacct atccatatga tgtgccagat tatgcagatt atccatatga tgtgccagat    1140
tatgcagatc tggcacgtac tgtaggagat gtgcgtcgtg ccgagcagct actgcaggat    1200
gcacggcggg caaggagctg ggctgaggat gagaaacaga aggcagagac agtacaggca    1260
gcactggagg aggcccagcg ggcacagggt attgcccagg gtgccatccg ggggcagtg    1320
gctgacacac gggacacaga gcagaccctg taccaggtac aggagaggat ggcaggtgca    1380
gagcgggcac tgagctctgc aggtgaaagg gctcggcagt tggatgctct cctggaggct    1440
ctgaaattga aacgggcagg aaatagtctg gcagcctcta cagcagaaga aacggcaggc    1500
agtgcccagg tcgtgcccca ggaggctgag cagctgctac gcggtcctct gggtgatcag    1560
taccagacgt tgaaggccct agctgagcgc aaggcccaag tgtgtgctgg ctgcacaggca    1620
agggcagaac aactgcggga tgaggctcgg gacctgttgc aagccgctca ggacaagctg    1680
cagcggctac aggaattgga aggcacctat gaggaaaatg agcgggcact ggagagtaag    1740
gcagcccagt tggacgggtt ggaggccagg atgcgcagcg tgcttcaagc catcaacttg    1800
caggtgcaga tctacaacac ctgccagtga                                     1830
```

MODIFIED LAMININ CONTAINING COLLAGEN BINDING MOLECULE AND USE THEREOF

TECHNICAL FIELD

The present invention relates to a modified laminin containing a collagen binding molecule; an extracellular-matrix material, a culture substrate, a scaffold each comprising the modified laminin; and a method for cell culture using the modified laminin.

BACKGROUND ART

Stem cells, in particular pluripotent stem cells such as ES cells and iPS cells, are receiving worldwide attention for their potential application to regenerative medicine. The culture and maintenance of stem cells without loss of their pluripotency usually requires the presence of feeder cells in their culture system, and as such feeder cells, mouse embryonic fibroblasts (MEFs) whose division has been arrested by radiation or antibiotic treatment are used. However, the use of feeder cells is a great restriction on clinical application of human stem cells.

For application of human stem cells to regenerative medicine, a feeder-free (no feeder cells are used) and xeno-free (no xenogeneic components are contained in the culture system) culture environment is required. The present inventors previously found that recombinant human laminins (particularly, laminin 332, which consists of α3, β3 and γ2 chains, and laminin 511, which consists of α5, β1 and γ1 chains) are effective for maintaining the pluripotency of human ES cells (see Non Patent Literature 1), and proposed that a recombinant human laminin E8 fragment or a modified laminin in which a cell adhesion molecule and/or a growth factor binding molecule is conjugated to the recombinant human laminin E8 fragment can be used as an extracellular matrix which enables maintenance culture of stem cells while supporting the retention of their pluripotency (see Patent Literature 1 and 2 and Non Patent Literature 2).

Following the maintenance culture of human stem cells, they should be differentiated to form a three-dimensional tissue structure for their application to regenerative medicine. In the case where cells isolated from a tissue are made to form a three-dimensional tissue structure, a conventionally used extracellular matrix is Matrigel (registered trademark), the trade name for a crude extract of mouse EHS sarcoma, which is known for excessive production of basement membrane components. However, Matrigel is of murine origin and thus is problematic in terms of safety for human use. Collagen gel is also widely used as an extracellular matrix for the three-dimensional culture system, but when collagen gel is used alone, the formation of a three-dimensional tissue structure from human stem cells is hardly achieved due to its poor ability to maintain stem cells. That is, under the current circumstances, there is no appropriate extracellular-matrix material to serve as an alternative to Matrigel for the formation of a three-dimensional tissue structure. Therefore, the speedy development of extracellular-matrix materials for the formation of a safe three-dimensional tissue structure for regenerative medicine in humans is strongly desired.

CITATION LIST

Patent Literature

Patent Literature 1: JP-A 2011-78370
Patent Literature 2: WO 2012-137970

Non Patent Literature

Non Patent Literature 1:
Miyazaki T, Futaki S, Hasegawa K, Kawasaki M, Sanzen N, Hayashi M, Kawase E, Sekiguchi K, Nakatsuji N, Suemori H. Recombinant human laminin isoforms can support the undifferentiated growth of human embryonic stem cells. Biochem. Biophys. Res. Commun. 375; 27-35, 2008.
Non Patent Literature 2:
Miyazaki. T, Futaki S, Suemori H, Taniguchi Y, Yamada M, Kawasaki M, Hayashi M, Kumagai H, Nakatsuji N, Sekiguchi K, Kawase E. Laminin E8 fragments support efficient adhesion and expansion of dissociated human pluripotent stem cells. Nature communications. DOI: 10.1038/ncomms2231, 2012.

SUMMARY OF INVENTION

Technical Problem

An object of the present invention is to provide an extracellular-matrix material which serves as an alternative to Matrigel and is useful for the formation of a safe three-dimensional tissue structure for regenerative medicine in humans.

Solution to Problem

The present invention includes the following to achieve the above-mentioned object.
(1) A modified laminin characterized in that a laminin or a heterotrimeric laminin fragment has a collagen binding molecule conjugated to at least one site selected from the α chain N-terminus, the β chain N-terminus and the γ chain N-terminus.
(2) The modified laminin according to the above (1), wherein the laminin or the heterotrimeric laminin fragment has the collagen binding molecules conjugated to two or more sites selected from the α chain N-terminus, the β chain N-terminus and the γ chain N-terminus.
(3) The modified laminin according to the above (1) or (2), wherein the laminin fragment has integrin binding activity.
(4) The modified laminin according to the above (3), wherein the laminin fragment is a laminin E8 fragment.
(5) The modified laminin according to any one of the above (1) to (4), wherein the laminin or the heterotrimeric laminin fragment consists of one kind of α chain selected from α1 to α5 or a fragment thereof, one kind of β chain selected from β1 to β3 or a fragment thereof, and one kind of γ chain selected from γ1 to γ3 or a fragment thereof.
(6) The modified laminin according to the above (5), wherein the laminin or the heterotrimeric laminin fragment is laminin α5β1γ1 or a fragment thereof, laminin α3β3γ2 or a fragment thereof, laminin α1β1γ1 or a fragment thereof, laminin α1β2γ1 or a fragment thereof, laminin α2β1γ1 or a fragment thereof, laminin α2β2γ1 or a fragment thereof, laminin α3β1γ1 or a fragment thereof, laminin α3β2γ1 or a fragment thereof, laminin α4β1γ1 or a fragment thereof, laminin α4β2γ1 or a fragment thereof, or laminin α5β2γ1 or a fragment thereof.

(7) The modified laminin according to any one of the above (1) to (6), wherein the collagen binding molecule is one or more kinds selected from (a) fibronectin or a fragment having a collagen binding domain thereof,
(b) collagenase or a fragment having a collagen binding domain thereof,
(c) integrin α1 chain or a fragment having a collagen binding domain thereof,
(d) integrin α2 chain or a fragment having a collagen binding domain thereof,
(e) integrin α10 chain or a fragment having a collagen binding domain thereof,
(f) integrin α11 chain or a fragment having a collagen binding domain thereof,
(g) platelet glycoprotein VI or a fragment having a collagen binding domain thereof,
(h) discoidin domain receptor 1 or a fragment having a collagen binding domain thereof,
(i) discoidin domain receptor 2 or a fragment having a collagen binding domain thereof,
(j) mannose receptor or a fragment having a collagen binding domain thereof,
(k) phospholipase A2 receptor or a fragment having a collagen binding domain thereof,
(l) DEC205 or a fragment having a collagen binding domain thereof,
(m) Endo180 or a fragment having a collagen binding domain thereof,
(n) von Willebrand factor or a fragment having a collagen binding domain thereof,
(o) MMP-2 or a fragment having a collagen binding domain thereof,
(p) MMP-9 or a fragment having a collagen binding domain thereof,
(q) leukocyte-associated immunoglobulin-like receptor 1 or a fragment having a collagen binding domain thereof, and
(r) leukocyte-associated immunoglobulin-like receptor 2 or a fragment having a collagen binding domain thereof.

(8) The modified laminin according to any one of the above (1) to (7), being of human origin.
(9) An extracellular-matrix material comprising the modified laminin according to any one of the above (1) to (8), and collagen and/or gelatin.
(10) A culture substrate coated with the modified laminin according to any one of the above (1) to (8), and collagen and/or gelatin.
(11) A scaffold comprising the modified laminin according to any one of the above (1) to (8), and collagen and/or gelatin.
(12) A method for culturing mammalian cells, being characterized by culturing the cells in the presence of the modified laminin according to any one of the above (1) to (8), and collagen and/or gelatin.
(13) The method according to the above (12), wherein the mammalian cells are ES cells, iPS cells or somatic stem cells.

Advantageous Effects of Invention

The present invention can provide an extracellular-matrix material, a culture substrate and a scaffold each of which is useful for the formation of a safe three-dimensional tissue structure for regenerative medicine in humans and comprises a modified laminin, and collagen and/or gelatin.

BRIEF DESCRIPTION OF DRAWINGS

FIG. 10 shows the results of non-reducing SDS-PAGE analysis of a collagen binding domain (CBD)-free laminin 311E8 fragment and laminin 311E8 fragments fused with one or two CBDs.

FIG. 11 shows the results of non-reducing SDS-PAGE analysis of a collagen binding domain (CBD)-free laminin 321E8 fragment and laminin 321E8 fragments fused with one or two CBDs.

DESCRIPTION OF EMBODIMENTS

<Modified Laminin>

Figure 1:
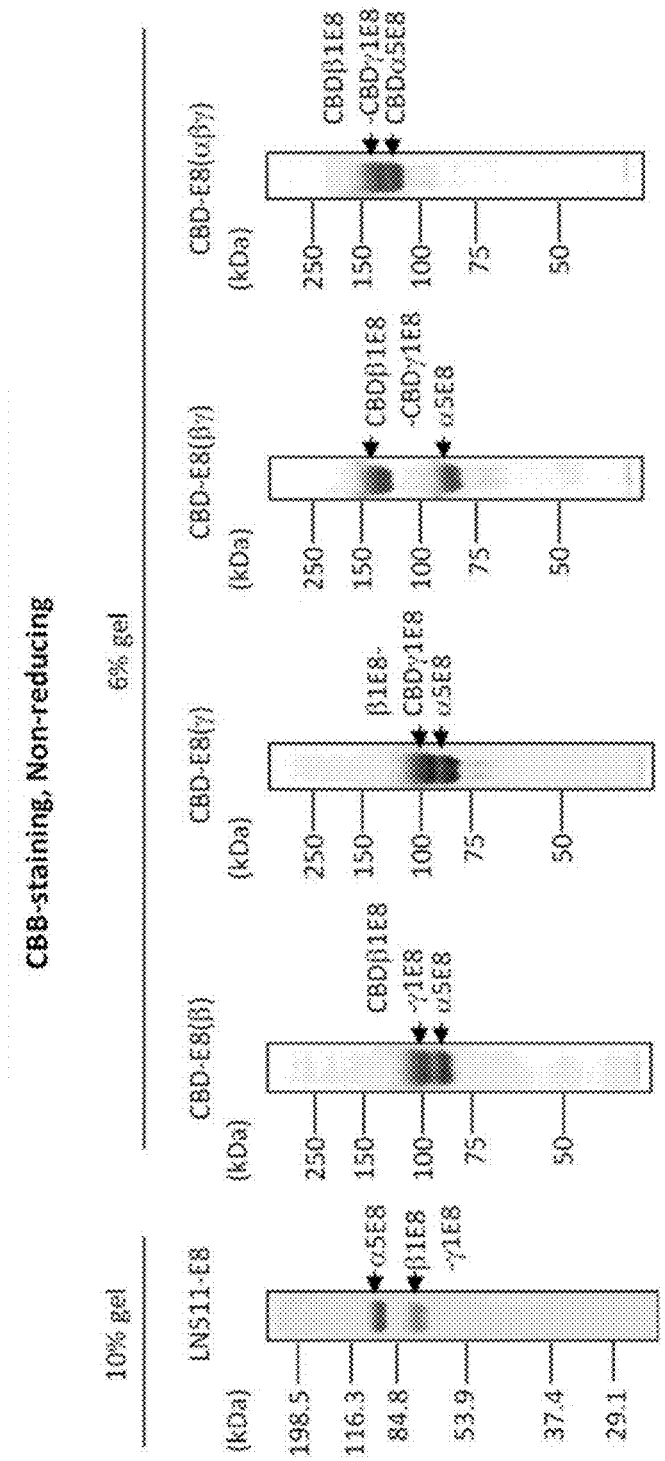
FIG. 1 shows the results of non-reducing SDS-PAGE analysis of a collagen binding domain (CBD)-free laminin 511E8 fragment and laminin 511E8 fragments fused with one, two or three CBDs.

The present invention provides a modified laminin characterized in that a laminin or a heterotrimeric laminin fragment has a collagen binding molecule conjugated to at least one site selected from the α chain N-terminus, the β chain N-terminus and the γ chain N-terminus.

Laminins are heterotrimeric molecules consisting of three subunits termed α, β and γ chains. Five kinds of α chains (α1 to α5), three kinds of β chains (β1 to β3) and three kinds of γ chains (γ1 to γ3) are known, and various combinations of these chains result in at least 12 kinds of laminin isoforms (see Table 1). The laminin which constitutes the modified laminin of the present invention may be any of these isoforms. That is, the laminin or the heterotrimeric laminin fragment which constitutes the modified laminin of the present invention consists of one kind of α chain selected from α1 to α5 or a fragment thereof, one kind of β chain selected from β1 to β3 or a fragment thereof, and one kind of γ chain selected from γ1 to γ3 or a fragment thereof. Specifically, the 12 kinds of isoforms shown in Table 1 and all the other possible isoforms and fragments thereof can preferably be used. Preferred are laminin α5β1γ1 or a fragment thereof, laminin α3β3γ2 or a fragment thereof, laminin α1β1γ1 or a fragment thereof, laminin α1β2γ1 or a fragment thereof, laminin α2β1γ1 or a fragment thereof, laminin α2β2γ1 or a fragment thereof, laminin α3β1γ1 or a fragment thereof, laminin α3β2γ1 or a fragment thereof, laminin α4β1γ1 or a fragment thereof, laminin α4β2γ1 or a fragment thereof, and laminin α5β2γ1 or a fragment thereof. More preferred are laminin α3β3γ2 or a fragment thereof, and laminin α5β1γ1 or a fragment thereof.

TABLE 1

| α chain | Trimer composition | |
|---|---|---|
| α1 | α1β1γ1 | (laminin-1) |
|  | α1β2γ1 | (laminin-3) |
| α2 | α2β1γ1 | (laminin-2) |
|  | α2β2γ1 | (laminin-4) |
|  | α2β1γ3 | (laminin-12) |
| α3 | α3β3γ2 | (laminin-5) |
|  | α3β1γ1 | (laminin-6) |
|  | α3β2γ1 | (laminin-7) |
| α4 | α4β1γ1 | (laminin-8) |
|  | α4β2γ1 | (laminin-9) |
| α5 | α5β1γ1 | (laminin-10) |
|  | α5β2γ1 | (laminin-11) |

The origin of the laminin is not particularly limited and laminins derived from various organisms can be used. Preferred are laminins derived from mammals, including but not limited to humans, mice, rats, cattle and pigs. Among these, a human laminin is particularly preferably used. In the culture of human stem cells for preparation of materials for human regenerative medicine, a xeno-free (no xenogeneic components are contained in the culture system) environment is required, and for this reason, a human laminin is preferably used.

The laminin which constitutes the modified laminin of the present invention may be a full-length laminin or a fragment thereof. That is, the laminin may be a full-length laminin consisting of a full-length α chain, a full-length β chain and a full-length γ chain, or a laminin fragment consisting of α, β and γ chains of which one or more are fragments shorter than the corresponding full-length chains. The laminin fragment needs to be in the form of a heterotrimer, and preferably has integrin binding activity. The heterotrimer formation of the laminin fragment can be confirmed from, for example, the number of bands detected by SDS-PAGE. The integrin binding activity of the laminin fragment can be confirmed by a solid phase binding assay etc.

The laminin fragment which constitutes the modified laminin of the present invention needs to be in the form of a heterotrimer consisting of α, β and γ chains, but the molecular weight etc. of the laminin fragment are not particularly limited. In terms of the strength of the integrin binding activity and the efficiency of recombinant expression (the recombinant protein yield is higher in comparison with that of a full-length laminin), a laminin E8 fragment is preferred. The laminin E8 fragment was identified as a fragment having the strongest cell adhesion activity among the fragments obtained by elastase digestion of mouse laminin α1β1γ1 (hereinafter referred to as "mouse laminin 111") (Edgar D., Timpl R., Thoenen H. The heparin-binding domain of laminin is responsible for its effects on neurite outgrowth and neuronal survival. EMBO J., 3: 1463-1468, 1984; and Goodman S L., Deutzmann R., von der Mark K. Two distinct cell-binding domains in laminin can independently promote nonneuronal cell adhesion and spreading. J. Cell Biol., 105: 589-598, 1987). It is presumed that elastase digestion of laminins other than mouse laminin 111 could produce fragments corresponding to the mouse laminin 111 E8 fragment, but there is no report on isolation or identification of such fragments. Therefore, the laminin E8 used in the present invention does not have to be an elastase-digested product of laminins, and may be any laminin fragment having the cell adhesion activity, structure and molecular weight equivalent to those of mouse laminin 111E8.

The laminin may be a native laminin or a mutant laminin that has a modification(s) of one or more amino acid residues but retains the biological activities of the native laminin. The method for producing the laminin is not particularly limited. For example, the laminin can be obtained by purification from highly laminin-expressing cells. Alternatively, the laminin can be produced as a recombinant protein. The method for producing the laminin fragment is not particularly limited either. For example, the laminin fragment can be obtained by digestion of a full-length laminin with a protease such as elastase, followed by isolation and purification of the fragment of interest. Alternatively, the laminin fragment can be produced as a recombinant protein. In terms of production quantity, quality uniformity, production cost, etc., it is preferred that the laminin and the laminin fragment are produced as a recombinant protein.

The recombinant laminin and the recombinant laminin fragment can be produced by appropriate known recombinant techniques, for example, by preparing DNAs encoding full-length or partial-length laminin α, β and γ chains, inserting the DNAs into separate expression vectors, cointroducing the three resulting expression vectors into appropriate host cells, and purifying the expressed trimeric protein by a known method. Examples of the method for producing the recombinant laminin (full-length laminin) include, but are not limited to, the method of Ido et al. (Hiroyuki Ido, Kenji Harada, Sugiko Futaki, Yoshitaka Hayashi, Ryoko Nishiuchi, Yuko Natsuka, Shaoliang Li, Yoshinao Wada, Ariana C. Combs, James M. Ervasti, and Kiyotoshi Sekiguchi, "Molecular dissection of the α-dystroglycan- and integrin-binding sites within the globular domain of human laminin-10" The Journal of Biological Chemistry, 279, 10946-10954, 2004). Examples of the method for producing the recombinant laminin fragment (laminin E8) include, but are not limited to, the method of Ido et al. (Hiroyuki Ido, Aya Nakamura, Reiko Kobayashi, Shunsuke Ito, Shaoliang Li, Sugiko Futaki, and Kiyotoshi Sekiguchi, "The requirement of the glutamic acid residue at the third position from the carboxyl termini of the laminin 7 chains in integrin binding by laminins" The Journal of Biological Chemistry, 282, 11144-11154, 2007).

Information regarding the nucleotide and amino acid sequences of the genes encoding α, β and γ chains which constitute laminins derived from major mammals can be obtained from known databases (e.g., GenBank). The accession numbers of the constituent chains of laminins derived from major mammals including humans are shown in Table 1. Information regarding the nucleotide and amino acid sequences of the constituent chains of laminins derived from other organisms can also be obtained from known databases (e.g., GenBank).

TABLE 2

| | Amino acid sequence | Nucleotide sequence |
|---|---|---|
| Human laminin α1 chain | NP_005550 | NM_005559 |
| Human laminin α2 chain | NP_000417 | NM_000426 |
| Human laminin α3 chain | NP_000218 | NM_000227 |
| Human laminin α4 chain | NP_002281 | NM_002290 |
| Human laminin α5 chain | NP_005551 | NM_005560 |
| Human laminin β1 chain | NP_002282 | NM_002291 |
| Human laminin β2 chain | NP_002283 | NM_002292 |
| Human laminin β3 chain | NP_000219 | NM_000228 |
| Human laminin γ1 chain | NP_002284 | NM_002293 |
| Human laminin γ2 chain | NP_005553 | NM_005562 |
| Human laminin γ3 chain | NP_006050 | NM_006059 |
| Mouse laminin α5 chain | NP_001074640 | NM_001081171 |
| Mouse laminin β1 chain | NP_032508 | NM_008482 |
| Mouse laminin γ1 chain | NP_034813 | NM_010683 |
| Rat laminin α5 chain | NP_001178538 | NM_001191609 |
| Rat laminin β1 chain | NP_001100191 | NM_001106721 |
| Rat laminin γ1 chain | NP_446418 | NM_053966 |

Laminin E8 is a trimeric fragment formed of a C-terminal fragment of the α chain lacking globular domains 4 and 5 (hereinafter referred to as "α chain E8"), a C-terminal fragment of the β chain (hereinafter referred to as "β chain E8"), and a C-terminal fragment of the γ chain (hereinafter referred to as "γ chain E8"), and the molecular weight of the trimer is about 150 to 170 kDa. The α chain E8 generally consists of about 770 amino acids, of which about 230 amino acids from the N-terminus are involved in the trimer formation. The β chain E8 generally consists of about 220 to 230 amino acids. The γ chain E8 generally consists of about 240 to 250 amino acids. The glutamic acid residue at the third position from the C-terminus of the γ chain E8 is essential for the cell adhesion activity of laminin E8 (Hiroyuki Ido, Aya Nakamura, Reiko Kobayashi, Shunsuke Ito, Shaoliang Li, Sugiko Futaki, and Kiyotoshi Sekiguchi, "The requirement of the glutamic acid residue at the third position from the carboxyl termini of the laminin γ chains in integrin binding by laminins" The Journal of Biological Chemistry, 282, 11144-11154, 2007).

The collagen binding molecule which constitutes the modified laminin of the present invention is not particularly limited as long as it is a molecule having a collagen binding domain. The collagen binding molecule may be a full-length molecule having a collagen binding domain, or a fragment having a collagen binding domain. The kind of the collagen as a binding target is not particularly limited and various kinds of collagens can be binding targets. Preferred are type I collagen, type II collagen, type III collagen, type IV collagen and type V collagen (Engvall et al., 1978, J. Exp. Med. 1584-1595, and Woodley et al., 1983, Biochemica et Biophysica Acta., 761, 278-283).

The collagen binding molecule is not particularly limited as long as it is a molecule capable of binding to collagens. Examples of the collagen binding molecule include the following (a) to (r):
(a) fibronectin or a fragment having a collagen binding domain thereof,
(b) collagenase or a fragment having a collagen binding domain thereof,
(c) integrin α1 chain or a fragment having a collagen binding domain thereof,
(d) integrin α2 chain or a fragment having a collagen binding domain thereof,
(e) integrin α10 chain or a fragment having a collagen binding domain thereof,
(f) integrin α11 chain or a fragment having a collagen binding domain thereof,
(g) platelet glycoprotein VI or a fragment having a collagen binding domain thereof,
(h) discoidin domain receptor 1 or a fragment having a collagen binding domain thereof,
(i) discoidin domain receptor 2 or a fragment having a collagen binding domain thereof,
(j) mannose receptor or a fragment having a collagen binding domain thereof,
(k) phospholipase A2 receptor or a fragment having a collagen binding domain thereof, (l) DEC205 or a fragment having a collagen binding domain thereof, (m) Endo180 or a fragment having a collagen binding domain thereof, (n) von Willebrand factor or a fragment having a collagen binding domain thereof, (o) MMP-2 or a fragment having a collagen binding domain thereof, (p) MMP-9 or a fragment having a collagen binding domain thereof, (q) leukocyte-associated immunoglobulin-like receptor 1 or a fragment having a collagen binding domain thereof, and (r) leukocyte-associated immunoglobulin-like receptor 2 or a fragment having a collagen binding domain thereof.

The origin of the collagen binding molecule is not particularly limited and collagen binding molecules derived from various organisms can be used. Preferred are collagen binding molecules derived from mammals, including but not limited to humans, mice, rats, cattle and pigs. Among these, collagen binding molecules of human origin are particularly preferably used. In the culture of human stem cells for preparation of materials for human regenerative medicine, a xeno-free (no xenogeneic components are contained in the culture system) environment is required, and for this reason, collagen binding molecules of human origin are preferably used.

The method for producing the collagen binding molecule is not particularly limited. For example, the collagen binding molecule can be obtained by purification from cells expressing a collagen binding molecule of interest. Alternatively, the collagen binding molecule can be produced as a recombinant protein. The recombinant protein can be produced by appropriate known recombinant techniques. Information regarding the nucleotide and amino acid sequences of the human genes encoding the above-listed collagen binding molecules (a) to (r) can be obtained from known databases (e.g., GenBank) with the use of the respective accession numbers shown in Table 3. Information regarding the nucleotide and amino acid sequences of the genes encoding collagen binding molecules derived from non-human organisms can also be obtained from known databases (e.g., GenBank).

TABLE 3

| | Amino acid sequence | Nucleotide sequence |
|---|---|---|
| Fibronectin | NP_997647 | NM_212482 |
| Collagenase | NP_002412 | NM_002421 |
| Integrin α1 chain | NP_852478 | NM_181501 |
| Integrin α2 chain | NP_002194 | NM_002203 |
| Integrin α10 chain | NP_003628 | NM_003637 |
| Integrin α11 chain | NP_001004439 | NM_001004439 |
| Platelet glycoprotein VI | NP_001077368 | NM_001083899 |
| Discoidin domain receptor 1 | NP_001945 | NM_001954 |
| Discoidin domain receptor 2 | NP_006173 | NM_006182 |
| Mannose receptor | NP_002429 | NM_002438 |
| Phospholipase A2 receptor | NP_031392 | NM_007366 |
| DEC205 | NP_002340 | NM_002349 |
| Endo180 | NP_006030 | NM_006039 |
| von Willebrand factor | NP_000543 | NM_000552 |
| MMP-2 | NP_004521 | NM_004530 |
| MMP-9 | NP_004985 | NM_004994 |
| Leukocyte-associated immunoglobulin-like receptor 1 | NP_002278 | NM_002287 |
| Leukocyte-associated immunoglobulin-like receptor 2 | NP_002279 | NM_002288 |

The location of the putative collagen binding domain in the amino acid sequence of each collagen binding molecule shown in Table 3 is as follows.

Fibronectin: Val1276-Thr604
Integrin α1 chain: Leu171-Ile351
Integrin α2 chain: Ile173-Lys353
Integrin α10 chain: Met166-Ile346
Integrin α11 chain: Met163-Ile341
Platelet glycoprotein VI: Pro26-Thr108
Discoidin domain receptor 1: Lys30-Cys185
Discoidin domain receptor 2: Cys30-Cys185
Mannose receptor: Asn162-Cys209
Phospholipase A2 receptor: Asn172-Cys219
DEC205: Asn163-Cys209
Endo180: Asn181-Cys228
von Willebrand factor: Leu1276-Gln1388 and Leu1690-Val1849 (2 locations)
MMP-2: Arg222-Ser396
MMP-9: Asn224-Cys388
Leukocyte-associated immunoglobulin-like receptor 1: Pro27-Val120
Leukocyte-associated immunoglobulin-like receptor 2: Pro27-Val120

In the modified laminin of the present invention, the above-described collagen binding molecule is conjugated to at least one site selected from the α chain N-terminus, the β chain N-terminus and the γ chain N-terminus of the laminin or the heterotrimeric laminin fragment, but is preferably conjugated to two or more of these sites. The modified laminin containing collagen binding molecules at two or three sites has remarkably higher collagen binding activity than that of the corresponding modified laminin containing a collagen binding molecule at one site. In the case where the collagen binding molecules are conjugated to two sites, the two sites are not particularly limited and may be any of the following combinations: the α chain N-terminus and the β chain N-terminus; the α chain N-terminus and the γ chain N-terminus; and the β chain N-terminus and the γ chain N-terminus. In the case where the collagen binding molecules are conjugated to two or more sites, the collagen binding molecules may be of one kind, or two or more kinds.

In the modified laminin of the present invention, a molecule other than the collagen binding molecule may be conjugated to the collagen binding molecule-unconjugated N-terminus of any constituent chain or conjugated to the α chain C-terminus. Examples of the molecule other than the collagen binding molecule include cell-growth regulatory molecules such as cell adhesion molecules and growth factor binding molecules (see Patent Literature 2).

The modified laminin of the present invention can be produced as a recombinant modified laminin by appropriate known recombinant techniques. For example, a modified laminin in which a collagen binding molecule is conjugated to the α chain N-terminus of laminin E8 can be produced as follows. First, a DNA encoding the laminin α chain E8 and a DNA encoding the collagen binding molecule are joined to give a fusion gene encoding a fusion protein in which the collagen binding molecule is conjugated to the α chain N-terminus of the laminin E8, and the fusion gene is inserted into an appropriate vector to give an expression vector. Subsequently, this expression vector, an expression vector for laminin β chain E8 and an expression vector for laminin γ chain E8 are co-transfected into appropriate host cells, and the expressed trimeric protein is purified by a known method. In a similar manner, modified laminins in which a cell adhesion molecule is conjugated to another site, and modified laminins in which cell adhesion molecules are conjugated to more than one site can also be produced. Alternatively, the modified laminin of the present invention can be produced by chemically conjugating a collagen binding molecule to at least one site selected from the α chain N-terminus, the β chain N-terminus and the γ chain N-terminus.

<Extracellular-Matrix Material>

The present invention provides an extracellular-matrix material comprising the modified laminin of the present invention, and collagen and/or gelatin. The extracellular-matrix material of the present invention may consist of the modified laminin and collagen, consist of the modified laminin and gelatin, consist of the modified laminin, collagen and gelatin, or contain these components and an additional component. The additional component is not particularly limited as long as it can be used for cell culture. For example, preferred are extracellular-matrix components other than collagen or gelatin. Examples of the extracellular-matrix components other than collagen or gelatin include fibronectin, Matrigel, proteoglycan, hyaluronic acid, tenascin, elastin, laminin and fibrinogen (fibrin).

The collagen and the gelatin used for the extracellular-matrix material of the present invention are not particularly limited and known collagens and gelatins used for cell culture can preferably be used. The extracellular-matrix material of the present invention can be provided in the form of a liquid, a gel, a sponge, a sheet or the like, and can be used for coating plates or as a three-dimensional matrix.

The extracellular-matrix material of the present invention contains a laminin as a suitable scaffold for stem cells, and thus can be used as a three-dimensional culture matrix for directed differentiation of stem cells leading to the formation of a three-dimensional tissue structure for regenerative medicine. In addition, the extracellular-matrix material of the present invention can be used not only for three-dimensional cell culture but also as an implantable device for guided tissue regeneration. Moreover, a three-dimensional culture environment optimized to directed differentiation of stem cells can be provided through conjugation of any laminin isoform to a three-dimensional collagen or gelatin matrix with a suitable stiffness.

<Culture Substrate>

The present invention provides a culture substrate coated with the modified laminin of the present invention, and collagen and/or gelatin. The cells to be cultured with the culture substrate of the present invention are not particularly limited and may be any cells that can be cultured. Mammalian cells are preferred, and mammalian stem cells are more preferred. The stem cells include somatic stem cells and pluripotent stem cells. Examples of the somatic stem cells include neural stem cells, mesenchymal stem cells, hematopoietic stem cells, cardiac stem cells, hepatic stem cells and small intestinal stem cells. Examples of the pluripotent stem cells include ES cells (embryonic stem cells), iPS cells (induced pluripotent stem cells), mGS cells (multipotent germ stem cells) and hybridomas of ES cells and somatic cells. Examples of the mammal as the origin of the cells include humans, mice, rats, cattle and pigs. Particularly preferred are humans. The culture substrate of the present invention is useful also in the case of feeder-free culture of cells that are conventionally cultured on feeder cells.

The method for producing the culture substrate of the present invention is not particularly limited. For example, a culture substrate may be coated with a mixed solution of collagen and/or gelatin, and the modified laminin. Alternatively, a culture substrate may be coated with collagen, gelatin or a mixture thereof, and subsequently with the modified laminin of the present invention. In the latter case, the modified laminin of the present invention is diluted with a suitable solvent, such as PBS, physiological saline and a physiological saline adjusted to a neutral pH with tris (hydroxymethyl)aminomethane or 4-(2-hydroxyethyl)-1-piperazine ethanesulfonic acid, followed by addition of the diluted solution onto a culture substrate coated with collagen and/or gelatin and subsequent incubation at about 4 to 37° C. for about 1 to 12 hours. As a result, the modified laminin is allowed to bind to the collagen or the gelatin and the coating is completed. A culture substrate for three-dimensional culture can also be produced by coating a culture substrate with collagen in a gel form and subsequently with the modified laminin. The culture substrate to be coated is not limited as long as it can be used for cell culture, and the examples include glass or plastic dishes, flasks, multiwell plates, culture slides and microcarriers, and polymer membranes such as a polyvinylidene fluoride membrane.

The collagen and the gelatin used for coating are not particularly limited and known collagens and gelatins used for cell culture can preferably be used. The collagen and the gelatin used for cell culture for regenerative medicine are preferably selected from collagens and gelatins confirmed safe for medical use, and preferably of human origin. Examples of the collagen and the gelatin certified safe for use in medicine include atelocollagen (KOKEN CO., LTD.), porcine skin collagen solution (Nipponham), Nippi high-grade gelatin (Nippi, Inc.) and MEDIGELATIN (Nippi, Inc.).

<Scaffold>

The present invention provides a scaffold for directed differentiation of stem cells leading to the formation of a three-dimensional tissue structure. The scaffold of the present invention is not particularly limited as long as it contains the modified laminin of the present invention, and collagen and/or gelatin. The component of the scaffold of the present invention may be any kind of material serving as a scaffold for cells, and is not particularly limited. Examples of the scaffold component include natural polymers such as collagen, gelatin, fibrin, hyaluronic acid, alginic acid, starch, chitin and pectic acid; self-assembling amphiphilic peptides; synthetic polymers such as polylactic acid, polyglycolic acid, a copolymer of lactic acid and glycolic acid, poly-ε-caprolactone, a copolymer of ε-caprolactone with lactic acid or glycolic acid, poly(citric acid), poly(malic acid), poly-α-cyanoacrylate, poly-β-hydroxybutyric acid, poly(trimethylene oxalate), poly(tetramethylene oxalate), poly(propylene carbonate), poly-γ-benzyl-L-glutamate, poly-γ-methyl-L-glutamate and poly-L-alanine; and inorganic materials such as hydroxyapatite and tricalcium phosphate. The scaffold may be in any three-dimensional form such as a gel, a sponge, a film, a mesh, a non-woven fabric and a knitted or woven fabric. Particularly, it is preferable that the scaffold is in a gel or film form with a fine network structure.

In the case where collagen or gelatin itself constitutes a scaffold (for example, collagen gel, collagen sponge, gelatin sponge, etc.), the modified laminin is made to bind thereto to give the scaffold of the present invention. In the case where a material other than collagen or gelatin constitutes a scaffold, the scaffold surface is coated with collagen and/or gelatin, and the modified laminin is made to bind to the collagen and/or the gelatin to give the scaffold of the present invention. The collagen and the gelatin that can be used for the scaffold of the present invention are the same as those used for the culture substrate of the present invention.

The scaffold of the present invention can preferably be used for three-dimensional culture of cells that can be cultured on the culture substrate of the present invention. The scaffold of the present invention contains a laminin as a suitable scaffold for stem cells, and thus is a very excellent three-dimensional culture scaffold for directed differentiation of stem cells leading to the formation of a three-dimensional tissue structure for regenerative medicine. In addition, the scaffold of the present invention can be used not only for three-dimensional cell culture but also as an implantable device for guided tissue regeneration.

<Method for Culturing Mammalian Cells>

The present invention provides a method for culturing mammalian cells in the presence of the modified laminin of the present invention, and collagen and/or gelatin. A culture method using collagen or gelatin bound to the modified laminin of the present invention as an extracellular matrix providing a scaffold for mammalian cells enables feeder-free culture of cells that are conventionally cultured on feeder cells. Moreover, this method enables stem cells with low affinity for collagen to be cultured on collagen and differentiated efficiently to form a three-dimensional tissue structure for regenerative medicine.

The culture method of the present invention is applicable to the culture of any mammalian cells, but is preferably applied to the culture of stem cells. The stem cells refer to cells having the self-renewal capacity and pluripotency, and include somatic stem cells and pluripotent stem cells. Examples of the somatic stem cells include neural stem cells, mesenchymal stem cells, hematopoietic stem cells, cardiac stem cells, hepatic stem cells and small intestinal stem cells. Examples of the pluripotent stem cells include ES cells (embryonic stem cells), iPS cells (induced pluripotent stem cells), mGS cells (multipotent germ stem cells) and hybridomas of ES cells and somatic cells. The mammal as the origin of the cells is not particularly limited, and the examples include humans, mice, rats, cattle and pigs. Particularly preferred are humans. That is, the culture method of the present invention is preferably used for human stem cell culture. In the case where the culture method of the present invention is used for human stem cell culture, the modified laminin of human origin is preferably used.

The culture method of the present invention is not particularly limited as long as it is a method for culturing mammalian cells in the presence of the modified laminin of the present invention, and collagen and/or gelatin. The examples include a culture method using a medium containing the modified laminin of the present invention, and collagen and/or gelatin as separate components; a culture method using a medium containing a complex of the modified laminin of the present invention and collagen, or a complex of the modified laminin of the present invention and gelatin; and a culture method using a culture substrate coated with collagen and/or gelatin, and a medium containing the modified laminin of the present invention. Preferred is a culture method using the culture substrate of the present invention or the scaffold of the present invention.

An embodiment in which human iPS cells are cultured according to the culture method of the present invention is described below. The culture method of the present invention is not limited to this embodiment and can also preferably be used for culture of mammalian cells other than human iPS cells.

(1) Collection of Human iPS Cells from Co-Culture System with Feeder Cells

Human iPS cells are collected from a co-culture system with feeder cells according to the following method 1 or 2.

Method 1:

To a culture dish in which human iPS cells have been co-cultured with feeder cells (for example, MEFs) (Day 3 to Day 5), 0.25% trypsin/DMEM-F12 (for example, 1 ml/60 mm dish) is added, and incubation was performed at 37° C. for 2 to 3 minutes. The culture dish is washed with DMEM-F12 and thereby feeder cells are removed. A culture medium is added to the culture dish and the cells on the entire culture dish are physically detached. By filtering the resulting cell suspension through a BD Falcon 100-μm cell strainer (BD Falcon #352460) and subsequently washing the strainer, only human iPS cell colonies are separated and collected.

Method 2:

To a culture dish in which human iPS cells have been co-cultured with feeder cells (for example, MEF's) (Day 3 to Day 5), a cell detachment solution (for example, Dissociation Solution for ES/iPS Cells (RCHETP002, ReproCELL Inc.), 1 mg/ml dispase/DMEM-F12, 10 mg/ml collagenase IV/DMEM-F12, etc.) (for example, 1 ml/60 mm dish) is added, and incubation was performed at 37° C. for 5 minutes to detach the human iPS cells and the MEFs from the culture dish. The detached cells are transferred into a 15-ml centrifuge tube. To this tube, about 10 ml of a culture medium is added, the cells are suspended, the tube is left to stand for 5 minutes to allow only the colonies to sediment, and then the supernatant is removed. By repeating this procedure twice or more, only human iPS cell colonies are sedimented and collected.

(2) Transfer of Human iPS Cells onto Culture Substrate of Present Invention

The collected human iPS cell colonies are dissociated into single cells. The method for dissociating the colonies into single cells is not particularly limited, and the examples include trypsinization and also include several times of flushing in a culture medium using a Pipetman P-1000 or the like. The dissociated single cells are resuspended in an appropriate culture medium (for example, TeSR2 etc.), and seeded on a culture dish coated with, for example, collagen and the modified laminin. The culture is performed in a CO concentration suitable for the culture medium used, and the culture medium is replaced daily.

(3) Passage Culture

Cultured cells are passaged at the time when the space available for cell expansion becomes limited or cell death becomes noticeable in the colonies. In the culture method of the present invention, passage may be performed by seeding human iPS cells in the state of properly-sized colonies, as in conventional methods. Alternatively, passage may be performed by seeding human iPS cells in a dissociated single-cell state. Here, the "dissociated single-cell state" means not only a state in which all the cells in a cell suspension are present as single cells, but also a state in which some cells in a cell suspension are present as single cells and other cells therein are present in an aggregate form of about several cells to a little more than ten cells.

In the Case where the Cells are Dissociated into Single Cells:

To a culture dish in which human iPS cells have been cultured, TrypLE Select (trade name, Invitrogen #12563011) (for example, 1 ml/100 mm dish) is added, and incubation was performed at 37° C. for 5 minutes. The human iPS cell colonies are dissociated into single cells, for example, by several times of flushing in a culture medium using a Pipetman P-1000 or the like. After addition of a culture medium, the human iPS cells are suspended and then collected in a centrifuge tube. After the step of centrifugation (1000×g, 3 minutes) and subsequent washing with a culture medium is repeated twice, the human iPS cells are resuspended in a fresh culture medium and seeded in a single-cell state at a cell density of, for example, about 40,000 cells/cm on a culture dish coated with the modified laminin of human origin (for example, 1.0 μg/cm$^2$). The culture is performed in a $CO_2$ concentration suitable for the culture medium used, and the culture medium is replaced daily.

In the Case where the Cells are not Dissociated into Single Cells:

In this case, collagenase IV, dispase, Accutase or the like is used as the enzyme for cell detachment. To a culture dish in which human iPS cells have been cultured, 10 mg/ml collagenase/DMEM-F12, 2 mg/ml dispase/DMEM-F12 or Accutase (Millipore #SCR005) (for example, 1 ml/60 mm dish) is added, and incubation was performed at 37° C. for 5 minutes. After removal of the enzyme solution, a culture medium is added, and the human iPS cell colonies are split into smaller-sized colonies composed of about 50 to 100 cells, for example, by several times of flushing in a culture medium using a Pipetman P-1000 or the like. The cell suspension is collected in a centrifuge tube. After the step of centrifugation (200×g, 3 minutes) and subsequent washing with a culture medium is repeated twice, the human iPS cells are resuspended in a fresh culture medium and seeded in a 2- to 4-fold dilution on a culture dish coated with the modified laminin of human origin (for example, 1.5 $\mu g/cm^2$). The culture is performed in a $CO_2$ concentration suitable for the culture medium used, and the culture medium is replaced daily.

The culture method of the present invention enables directed differentiation of stem cells into various somatic cells. The protocol for directed differentiation is not particularly limited, and any known protocol therefor can be selected as appropriate. Hereinafter, an exemplary protocol for directed differentiation of pluripotent stem cells and an exemplary protocol for directed differentiation of somatic stem cells are described, but these are non-limiting examples.

(i) Protocol for Hepatic Differentiation of Human ES or iPS Cells

Human ES or iPS cells are dissociated into single cells by Accutase (Millipore) and cultured for 2 days on Matrigel in a differentiation medium (a hESF-DIF medium (Cell Science & Technology Institute) supplemented with 10 μg/ml human recombinant insulin, 5 μg/ml human apotransferrin, 10 μM 2-mercaptoethanol, 10 μM sodium selenate and 0.5 mg/ml bovine serum albumin) supplemented with 100 ng/ml activin A and 10 ng/ml basic fibroblast growth factor (bFGF). The resulting mesendoderm cells are transduced with an adenovirus vector for FOXA2 gene expression and cultured on Matrigel in the same manner as above until day 6 for differentiation into definitive endoderm cells. These cells are transduced with an adenovirus vector for FOXA2 gene expression and an adenovirus vector for HNF1α gene expression and cultured for another 3 days on Matrigel in a hepatocyte culture medium (HCM, Lonza) supplemented with 30 ng/ml bone morphogenetic protein 4 (BMP4) and 20 ng/ml FGF4 for differentiation into hepatoblasts. These hepatoblasts are transduced with an adenovirus vector for FOXA2 gene expression and an adenovirus vector for HNF1α gene expression and cultured for 3 days on Matrigel in an HCM medium supplemented with 10 ng/ml HGF, 10 ng/ml FGF1, 10 ng/ml FGF4 and 10 ng/ml FGF10 for differentiation into hepatic progenitor cells. For hepatic maturation, these cells are cultured for 8 days on Matrigel in a L15 medium (Invitrogen) supplemented with 8.3% tryptose phosphate broth (BD), 10% FBS, 10 μM hydrocortisone 21-hemisuccinate, 1 μM insulin, 25 mM $NaHCO_3$, 20 ng/ml HGF, 20 ng/ml oncostatin M and 10 μM dexamethasone. This directed differentiation protocol reportedly allows the generation of hepatocyte-like cells with drug metabolizing capacity (reference: Takayama et al., J. Hepatology, 2012, 57, 628-636). This protocol can be performed using, instead of Matrigel, a three-dimensional matrix composed of a combination of the modified laminin of the present invention and a collagen gel, thereby providing safe hepatic cells for regenerative medicine in humans.

(ii) Protocol for Hepatic Differentiation of Somatic Stem Cells

Delta-like leucine zipper kinase (Dlk)-positive mouse fetal hepatic cells are cultured on EHS-laminin. The cells, which are designated as HPPL (hepatic progenitor cells proliferating on laminin), are seeded on 6-well plates at $2 \times 10^5$ cells/well and cultured until confluency. The medium is replaced with a DMEM/F12 medium supplemented with 20 ng/ml oncostatin M and the culture is continued for 5 days. Subsequently, the medium is replaced with 300 μl of Matrigel diluted 6-fold in DMEM/F12 medium, which forms a gel onto the cell layer. After additional 5 days of culture, the production of polysaccharides and the generation of PAS-positive hepatic cells are observed as described in the report (reference: Tanimizu et, al., J. Cell Sci., 2004, 117, 6425-6434). This protocol can be performed using, instead of the HPPL cells and the EHS gel, human stem cells and a three-dimensional matrix composed of a combination of the modified laminin of the present invention and a collagen gel, thereby providing safe hepatic cells for regenerative medicine in humans.

(iii) Protocol for Differentiation of Somatic Stem Cells into Cholangiocytes

The HPPL cells are cultured for 2 days on a 20% Matrigel-containing type I collagen gel on the upper surface of a 1-cm diameter culture insert. Subsequently, a gel of the same composition is cast on the cells and left to stand at 37° C. for 2 hours for solidification. To the upper and bottom chambers of the culture insert, 500 μl each of a DMEM/F12 medium supplemented with 5 ng/ml each of EGF and HGF is added. After 2 to 3 days of culture, the formation of tubular structures and the expression of a cholangiocyte marker cytokeratin 19 are observed as described in the report (reference: Tanimizu et al., Mol. Biol. Cell, 2009, 20, 2486-2494). This protocol is called "sandwich culture." The sandwich culture can be performed using, instead of the HPPL cells and Matrigel, human stem cells and a three-dimensional matrix composed of a combination of the modified laminin of the present invention and a collagen gel, thereby providing safe cholangiocytes for regenerative medicine in humans.

(iv) Three-Dimensional Culture of Small Intestinal Stem Cells

From mouse small intestinal crypts, Lgr5-positive cells are collected in a crypt culture medium (an Advanced DMEM/F12 medium supplemented with 10 to 50 ng/ml EGF, 500 ng/ml R-spondin 1 and 100 ng/ml noggin), and embedded one by one into 5 μl of Matrigel containing 1 μM Jagged-1 peptide (AnaSpec). To this, 100 μl of a crypt culture medium supplemented with 10 μM Y-27632 is added. The growth factors are added to the medium every other day, and the entire medium is replaced with a fresh one every four days. After the culture under such conditions is continued for 1 to 2 weeks, the reconstruction of the crypt structure is observed as described in the report (reference: Sato et al., Nature, 2009, 459, 262-265). This protocol can be performed using, instead of the mouse small intestinal stem cells and Matrigel, human cells and a three-dimensional matrix composed of a combination of the modified laminin of the present invention and a collagen gel, thereby enabling three-dimensional culture of safe small intestinal cells for regenerative medicine in humans.

EXAMPLES

Hereinafter, the present invention will be illustrated in detail by examples, but is not limited thereto.

Example 1: Preparation of Recombinant Proteins Composed of Laminin 511E8 Fused with Collagen Binding Domain of Human Fibronectin For preparation of recombinant proteins composed of laminin 511E8 fused with the collagen binding domain of human fibronectin (hereinafter, referred to as "CBD"), an expression vector for human laminin α5 chain E8, an expression vector for human laminin β1 chain E8, an expression vector for human laminin γ1 chain E8, an expression vector for human laminin α5 chain E8 fused with an N-terminal CBD, an expression vector for human laminin β1 chain E8 fused with an N-terminal CBD, and an expression vector for human laminin γ1 chain E8 fused with an N-terminal CBD were prepared, and these vectors were co-transfected in a given combination into host cells for expression of a recombinant protein of interest.

(1) Construction of Expression Vectors

A fragment composed of a cDNA encoding human laminin α5E8 (accession number: NP_005551 (see Table 2), Ala2534-Ala3327) and a 6×His tag-encoding DNA fused to the 5' end of the cDNA, a fragment composed of a cDNA encoding human laminin β1E8 (accession number: NP_002282 (see Table 2), Leu1561-Leu1786) and an HA tag-encoding DNA fused to the 5' end of the cDNA, and a fragment composed of a cDNA encoding human laminin γ1E8 (accession number: NP_002284 (see Table 2), Asn1364-Pro1609) and a FLAG tag-encoding DNA fused to the 5' end of the cDNA were separately amplified by PCR. These amplified fragments were separately inserted in the HindIII/EcoRV site (for α5E8) or the HindIII/EcoRI site (for β1E8 and γ1E8) of a pSecTag2B vector (Invitrogen) to give pSec-LNα5E8, pSec-LNβ1E8 and pSec-LNγ1E8 (Ido H. et al., J. Biol. Chem. 2007, 282, 11144-11154). A cDNA encoding CBD (accession number: NP_997647 (see Table 3), Val276-Thr604) was amplified by PCR to give a product with a 5'-end HindIII site. A fragment composed of a human laminin α5E8-encoding cDNA and a 6×His tag-encoding DNA fused to the 5' end of the cDNA, a fragment composed of a human laminin β1E8-encoding cDNA and an HA tag-encoding DNA fused to the 5' end of the cDNA, and a fragment composed of a human laminin γ1E8-encoding cDNA and a FLAG tag-encoding DNA fused to the 5' end of the cDNA were separately amplified by PCR, and then separately fused to the CBD-encoding DNA fragment by PCR. The resulting fragments were separately inserted into the HindIII/ClaI site of the pSec-LNα5E8 (for α5E8) or the HindIII/EcoRI site of a pSecTag2B vector (Invitrogen) (for β1E8 and γ1E8) to give pSec-CBD-LNα5E8, pSec-CBD-LNβ1E8 and pSec-CBD-LNγ1E8.

The amino acid sequence of a protein expressed by the pSec-CBD-LNα5E8 (CBD-LNα5E8) is shown in SEQ ID NO: 1, and the nucleotide sequence of the corresponding DNA (contained in the pSec-CBD-LNα5E8) is shown in SEQ ID NO: 2. The amino acid sequence of a protein expressed by the pSec-CBD-LNβ1E8 (CBD-LNβ1E8) is shown in SEQ ID NO: 3, and the nucleotide sequence of the corresponding DNA (contained in the pSec-CBD-LNβ1E8) is shown in SEQ ID NO: 4. The amino acid sequence of a protein expressed by the pSec-CBD-LNγ1E8 (CBD-LNβ1E8) is shown in SEQ ID NO: 5, and the nucleotide sequence of the corresponding DNA (contained in the pSec-CBD-LNγ1E8) is shown in SEQ ID NO: 6.

(2) Expression and Purification of Recombinant CBD-Fused Laminin 511E8 Fragments Recombinant CBD-fused laminin 511E8 fragments and a recombinant laminin 511E8 fragment were prepared using the FreeStyle™ 293 Expression System (Invitrogen). In each case, FreeStyle™ 293-F cells were transfected with a given combination of three kinds of expression vectors (see Table 1) using 293fectin (Invitrogen) and grown in serum-free FreeStyle™ 293 expression medium for 72 hours. The conditioned medium was collected and clarified by centrifugation. The clarified conditioned medium was first subjected to affinity chromatography using Ni-NTA-agarose. After column washing with TBS, the bound protein was eluted with a TBS containing 200 mM imidazole. Next, the imidazole eluate was applied to an anti-FLAG M2-agarose column, and the bound protein was eluted with 100 μg/ml FLAG peptide in TBS. The eluted protein was dialyzed against PBS. The dialyzed product was sterilized by filtration through a 0.22-μm disk syringe filter (Millipore, #SLGV033RS) and the filtrate was stored at −80° C. The combinations of the expression vectors used for the preparation of the recombinant CBD-fused laminin 511E8 fragments and the recombinant laminin 511E8 fragment are shown in Table 4.

TABLE 4

| | α5E8 expression vector | β1E8 expression vector | γ1E8 expression vector |
|---|---|---|---|
| LN511-E8 | LNα5E8 | LNβ1E8 | LNγ1E8 |
| CBD-E8(β) | LNα5E8 | CBD-LNβ1E8 | LNγ1E8 |
| CBD-E8(γ) | LNα5E8 | LNβ1E8 | CBD-LNγ1E8 |
| CBD-E8(βγ) | LNα5E8 | CBD-LNβ1E8 | CBD-LNγ1E8 |
| CBD-E8(αβγ) | CBD-LNα5E8 | CBD-LNβ1E8 | CBD-LNγ1E8 |

(3) SDS-PAGE Analysis of Recombinant CBD-Fused Laminin 511E8 Fragments

The concentrations of the purified proteins were determined by the BCA assay using bovine serum albumin (BSA) as a standard. The purities of the purified proteins were determined by non-reducing SDS-PAGE and subsequent Coomassie Brilliant Blue staining.

The results of the SDS-PAGE are shown in FIG. 1. In each sample, two bands corresponding to a monomer of α5 chain E8 and a dimer of β1 chain E8 and γ1 chain E8 were detected under non-reducing conditions, revealing that the recombinant laminin 511E8 fragment and the recombinant CBD-fused laminin 511E8 fragments were successfully purified as heterotrimeric proteins.

Example 2: Examination on Collagen or Gelatin Binding Activities of CBD-Fused Laminin 511E8 Fragments (1) Binding Activity Measurement Type I collagen (Nitta Gelatin Inc., type I-A: porcine origin) or gelatin (Sigma, G1890-100G: porcine origin) was diluted at 10 μg/ml in 0.1 M NaHCO₃, and a 96-well immuno plate (Nunc Maxisorp) was coated with 50 μl/well of the diluted solution at 4° C. overnight. The coating solution on the plate was removed, a TBS containing 1% BSA was added to the plate, and incubation was performed at room temperature for 2 hours for blocking. After this, the plate was washed twice with a TBS containing 0.1% BSA and 0.02% Tween-20 (hereinafter, referred to as "wash buffer"). Subsequently, each CBD-fused laminin 511E8 was diluted at various concentrations in a wash buffer, the diluted solutions were added and the plate was incubated with agitation at room temperature for 3 hours. The plate was washed 3 times with a wash buffer and then an anti-laminin α5 antibody 5D6-containing antiserum diluted 3000-fold in a wash buffer was added at 50 µl/well. The plate was incubated with agitation at room temperature for 1 hour and then washed 3 times with a wash buffer. An HRP-labeled anti-mouse IgG antibody diluted 3000-fold in a wash buffer was added at 50 µl/well and the plate was incubated with agitation at room temperature for 1 hour. The plate was washed 3 times with a wash buffer and an o-phenylenediamine solution was added at 50 µl/well for color development. The color development was stopped with the addition of 50 µl/well of 2.5 M sulfuric acid and the absorbance at 490 nm was measured.

(2) Experimental Results

Figure 2:
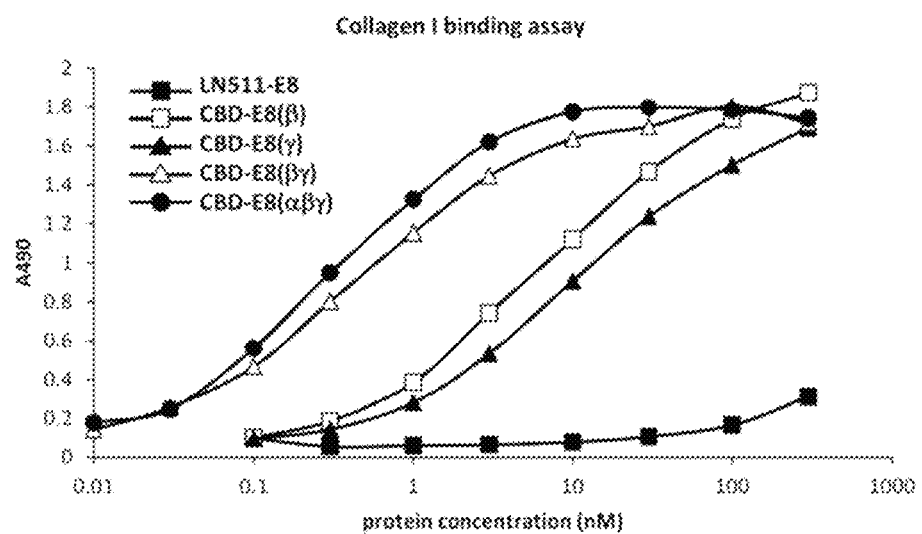
FIG. 2 shows the results on collagen binding activities of the collagen binding domain (CBD)-free laminin 511E8 fragment and the laminin 511E8 fragments fused with one, two or three CBDs.

The results on type I collagen binding activities are shown in FIG. 2. The CBD-free laminin 511E8 (indicated as LN511-E8 in the figure) hardly bound to type I collagen, but CBD-E8 (β) and CBD-E8 (γ), which contained a single CBD fused to the β1 or γ1 chain, were remarkably capable of binding to type I collagen. In addition, CBD-E8 (βγ), which contained CBDs fused to both the β1 and γ1 chains, and CBD-E8 (αβγ), which contained CBDs fused to all the three chains (α, β and γ chains), bound to type I collagen at lower concentrations as compared with the single CBD-fused E8 fragments, and the binding activities reached saturation at 10 nM. These results showed that the type I collagen binding activities of the forms with two or more CBDs (divalent or higher valent forms) were higher by approximately one order of magnitude than those of the forms with a single CBD (monovalent forms). However, no difference was found between the divalent form and the trivalent form. In addition, CBD-E8 (αβ), which contained CBDs fused to both the α5 and β1 chains, CBD-E8 (αγ), which contained CBDs fused to both the α5 and γ1 chains, had binding activities equivalent to that of CBD-E8 (βγ) (data not shown).

Figure 3:
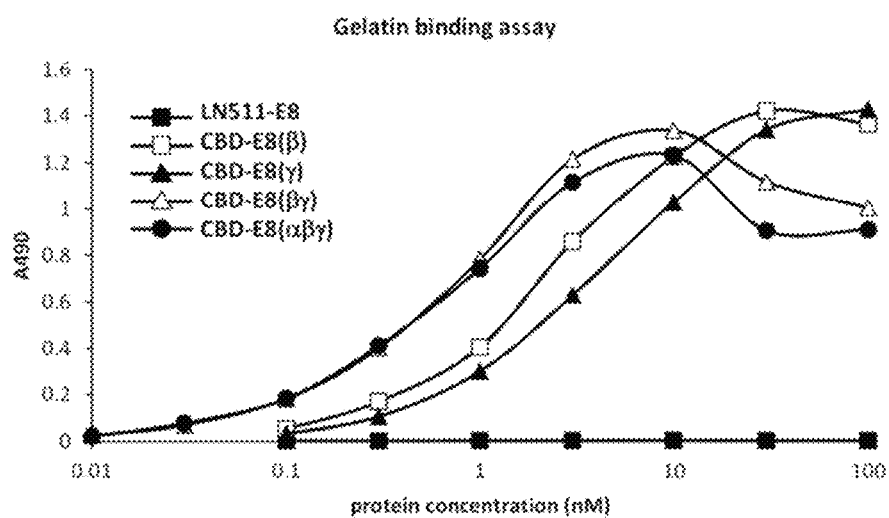
FIG. 3 shows the results on gelatin binding activities of the collagen binding domain (CBD)-free laminin 511E8 fragment and the laminin 511E8 fragments fused with one, two or three CBDs.

The results on gelatin binding activities are shown in FIG. 3. As is the case with the type I collagen binding activity, the CBD-free LN511-E8 hardly bound to gelatin, but the CBD-fused LN511-E8 fragments were remarkably capable of binding to gelatin, and the binding activities of the divalent or higher valent forms were approximately 3-fold stronger than those of the monovalent forms.

Example 3: Human iPS Cell Culture Using CBD-Fused Laminin 511E8 Fragments (1) Human iPS Cells The human iPS cells used were a cell line (clone name: tic (JCRB1331)) purchased from the Japanese Collection of Research Bioresources (JCRB) Cell Bank, the National Institute of Biomedical Innovation. The tic cells were maintained in co-culture with mouse feeder cells according to the method recommended by the JCRB Cell Bank, the National Institute of Biomedical Innovation. To the co-culture dish, 1 U/ml dispase/DMEM-F12 was added and colonies of the tic cells were harvested with a scraper. By filtrating the cell suspension containing the tic cell colonies and the mouse feeder cells through a BD Falcon 100-µm cell strainer and subsequently washing the cell strainer, the tic cell colonies were separated. The colonies remaining in the cell strainer were collected in a mTeSR1 (trade name, STEMCELL TECHNOLOGIES) medium, split into smaller colonies with the use of a Pipetman P-1000, resuspended in a mTeSR1 medium and seeded on a Matrigel-coated culture substrate. Expansion culture was performed at 37° C. in a 5% $CO_2$ atmosphere for 4 to 5 days. During the expansion culture, the culture medium was replaced daily. After the expansion culture, the cells were used for the experiments.

(2) Culture Method

A solution of type I collagen (Nitta Gelatin Inc., type I-C: porcine origin) diluted at 200 µg/ml in PBS, or 0.1% gelatin (Sigma) was added to a 12-well plate at 1 ml/well, and incubation was performed at 37° C. for 1 hour. For the collagen-coated plate, the collagen solution was subsequently aspirated off, 0.1% gelatin was added at 1 ml/well, and incubation was performed at 37° C. for 2 hours for blocking. The gelatin solution on each plate was removed and the plate was washed twice with PBS. Various laminin E8 fragments were separately diluted at 8 nM in PBS, the diluted solutions were added at 1 ml/well, and incubation was performed at 4° C. overnight. After this, the plate was washed 3 times with PBS.

The culture medium of the above-described iPS cells cultured on a Matrigel-coated dish (10 cm) was aspirated off, a PBS containing 4.8 mM EDTA was added, and incubation was performed at room temperature for 3 minutes. The EDTA solution was removed, TrypLE Express (Gibco) was added at 1 ml per dish, and incubation was performed at 37° C. for 1 minute to detach the iPS cells. The cells were suspended in a mTeSR1 medium (STEMCELL TECHNOLOGIES) containing supplements, transferred into a 15-ml tube, and centrifuged at 1000 rpm for 3 minutes. The supernatant was aspirated off and the cells were suspended at a concentration of $7.6 \times 10^4$ cells/ml in a mTeSR1 medium containing supplements. The PBS on the plate was aspirated off and the iPS cells were seeded on the plate at 1 ml/well. The plate was placed in an incubator with 5% $CO_2$ at 37° C. for cell culture. The duration of the cell culture was 3 days, during which the culture medium was replaced daily.

(3) Experimental Results

Figure 4:
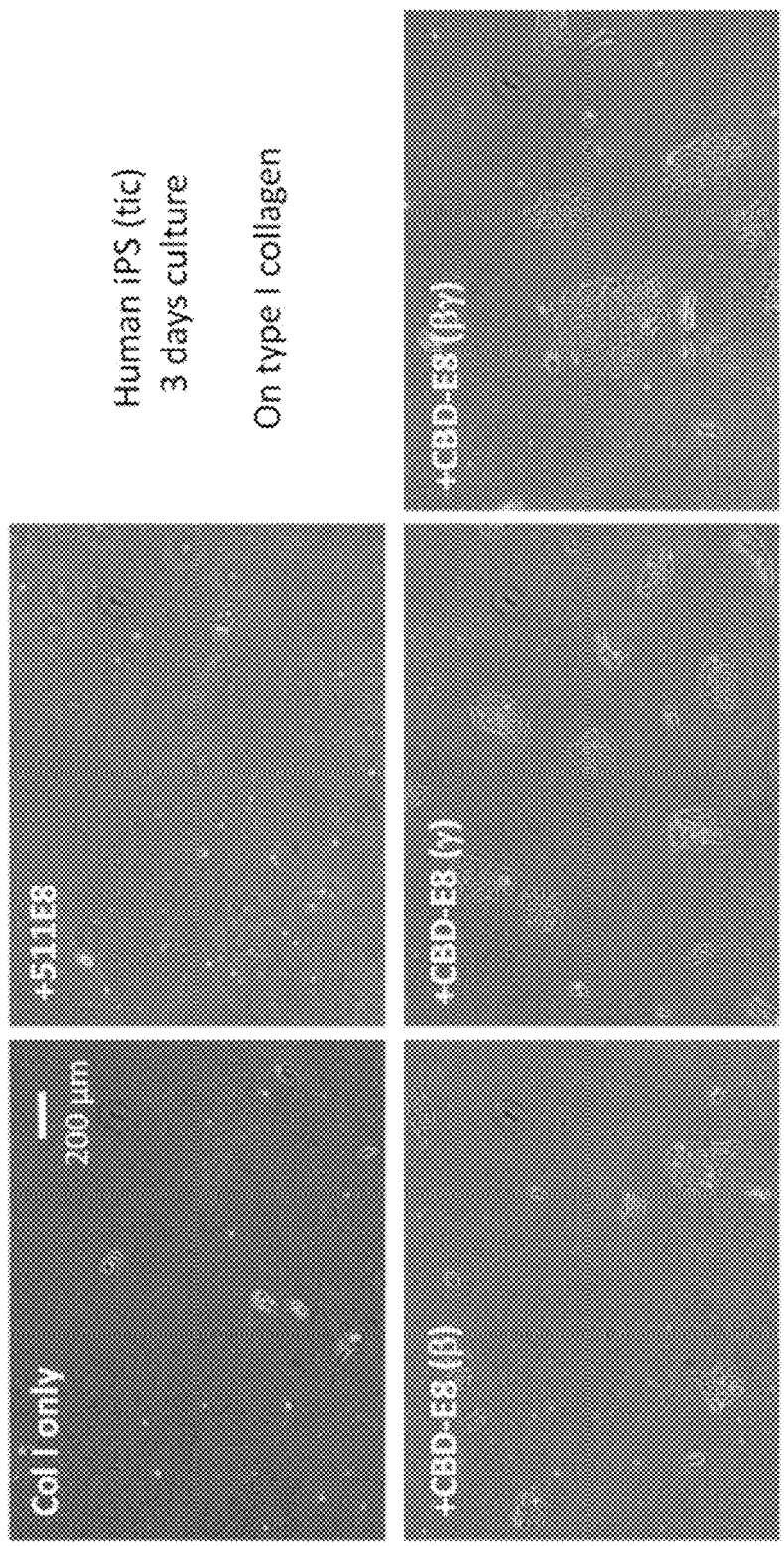
FIG. 4 shows the results of human iPS cell culture on a type I collagen-coated plate containing the three different kinds of collagen binding domain (CBD)-fused laminin 511E8 fragments and the laminin 511E8 fragment.

The images of the iPS cells on day 3 of culture under type I collagen-coating conditions are shown in FIG. 4. As is clear from FIG. 4, the iPS cells hardly proliferated when seeded on the plate coated only with type I collagen (indicated as "Col I only" in the figure). Similarly, the iPS cells hardly proliferated when seeded on the plate coated additionally with the CBD-free LN511-E8 (indicated as "+511E8" in the figure). However, when the plates were coated additionally with the LN511-E8 fused with a single CBD (indicated as "+CBD-E8 (β)" and "+CBD-E8 (γ)" in the figure), the iPS cells slightly proliferated. On the plate coated additionally with the LN511-E8 fused with two CBDs (indicated as "+CBD-E8 (βγ)" in the figure), the number of iPS cells was greater than those observed on the plates coated additionally with the LN511-E8 fused with a single CBD.

Figure 5:
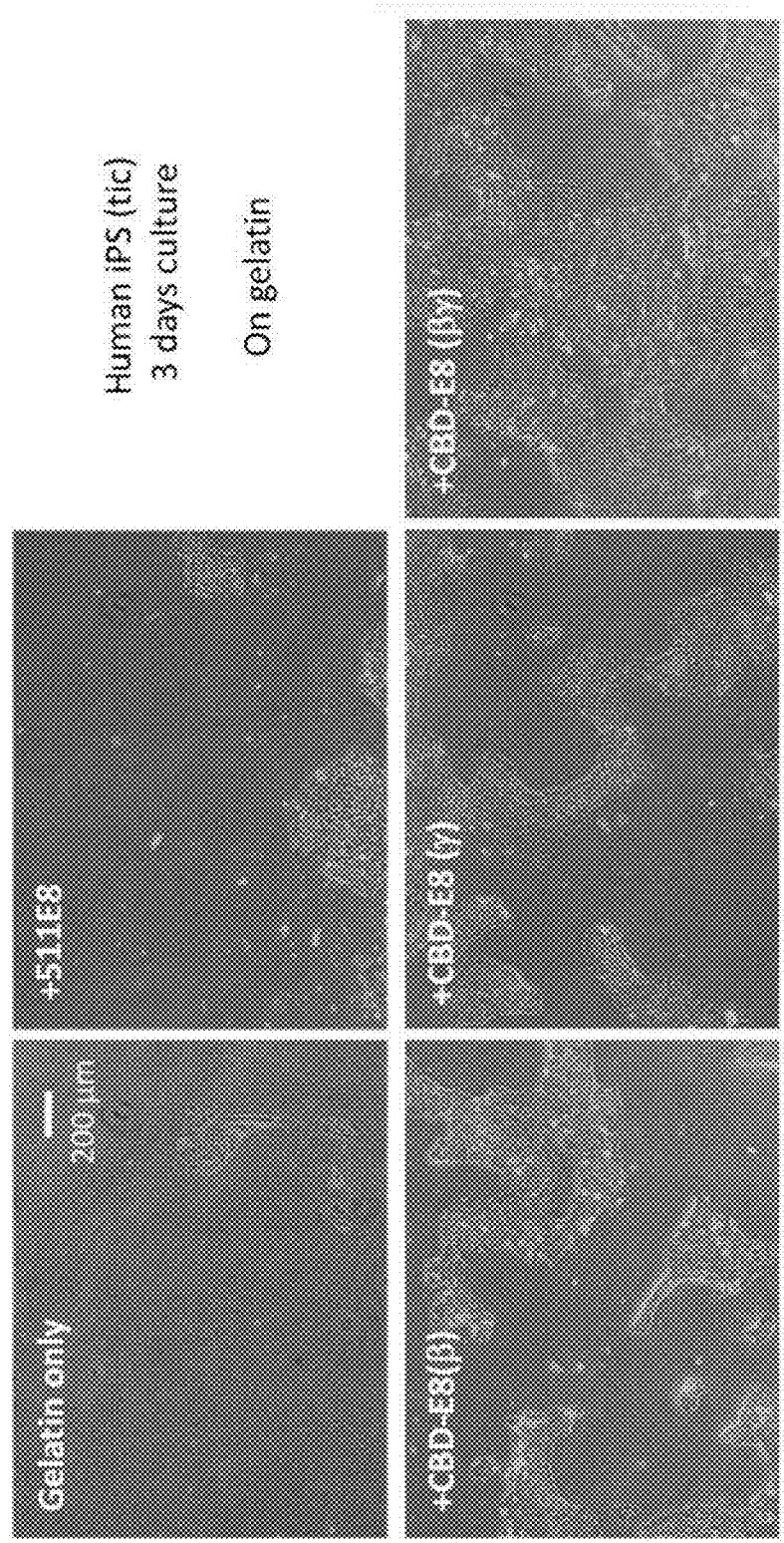
FIG. 5 shows the results of human iPS cell culture on a gelatin-coated plate containing the three different kinds of collagen binding domain (CBD)-fused laminin 511E8 fragments and the laminin 511E8 fragment.
Figure 6:
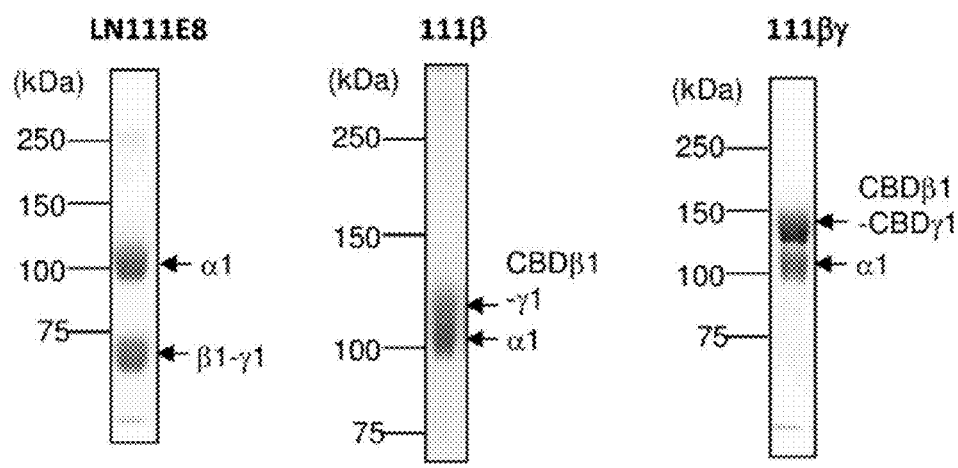
FIG. 6 shows the results of non-reducing SDS-PAGE analysis of a collagen binding domain (CBD)-free laminin 111E8 fragment and laminin 111E8 fragments fused with one or two CBDs.
Figure 7:
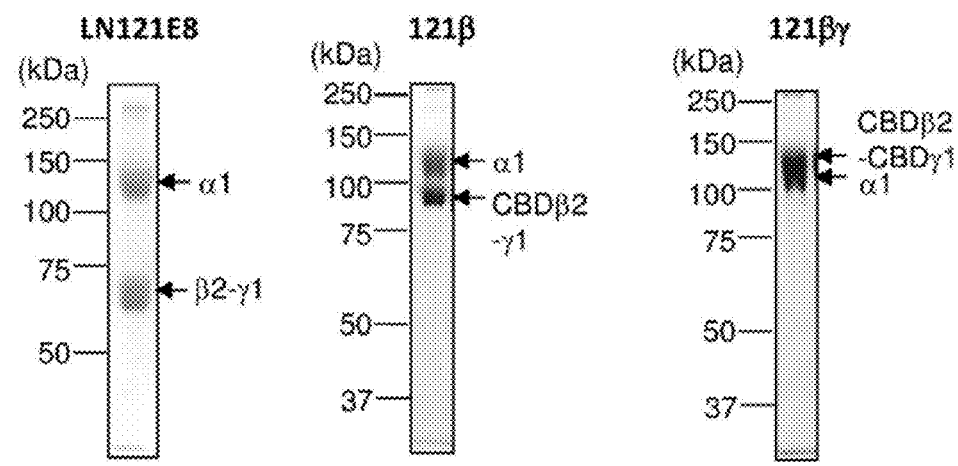
FIG. 7 shows the results of non-reducing SDS-PAGE analysis of a collagen binding domain (CBD)-free laminin 121E8 fragment and laminin 121E8 fragments fused with one or two CBDs.
Figure 8:
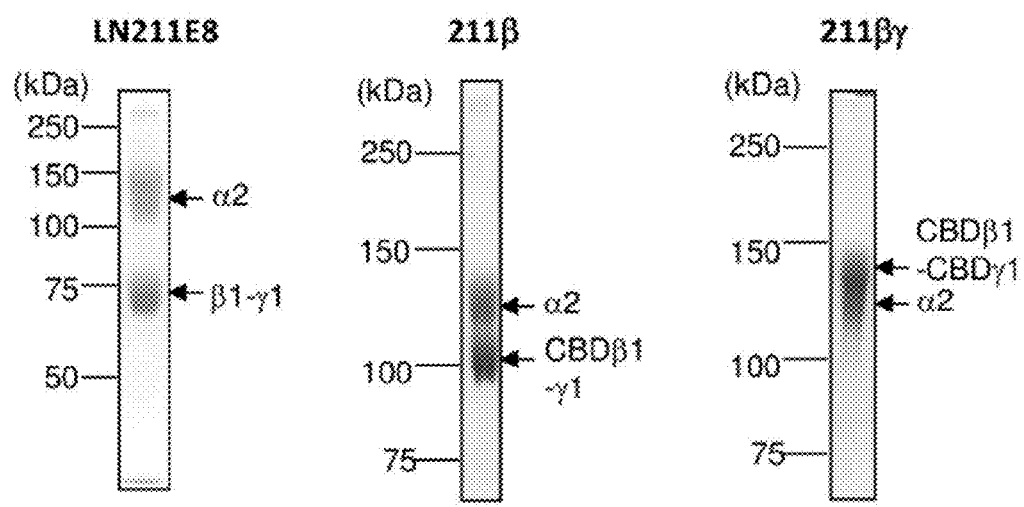
FIG. 8 shows the results of non-reducing SDS-PAGE analysis of a collagen binding domain (CBD)-free laminin 211E8 fragment and laminin 211E8 fragments fused with one or two CBDs.
Figure 9:
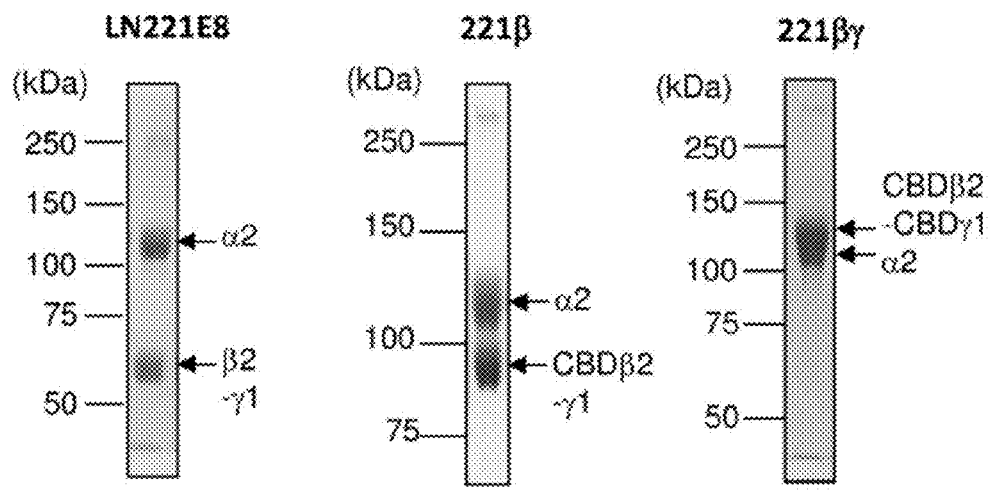
FIG. 9 shows the results of non-reducing SDS-PAGE analysis of a collagen binding domain (CBD)-free laminin 221E8 fragment and laminin 221E8 fragments fused with one or two CBDs.
Figure 12:
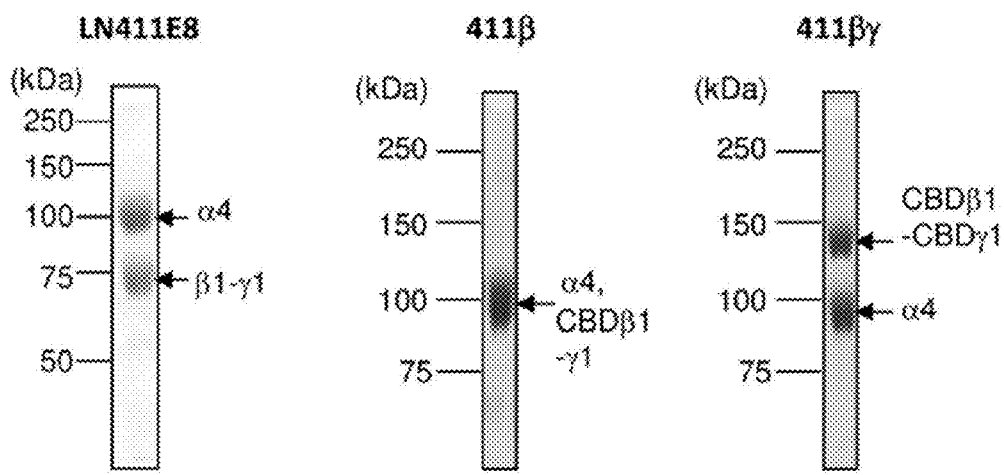
FIG. 12 shows the results of non-reducing SDS-PAGE analysis of a collagen binding domain (CBD)-free laminin 411E8 fragment and laminin 411E8 fragments fused with one or two CBDs.
Figure 13:
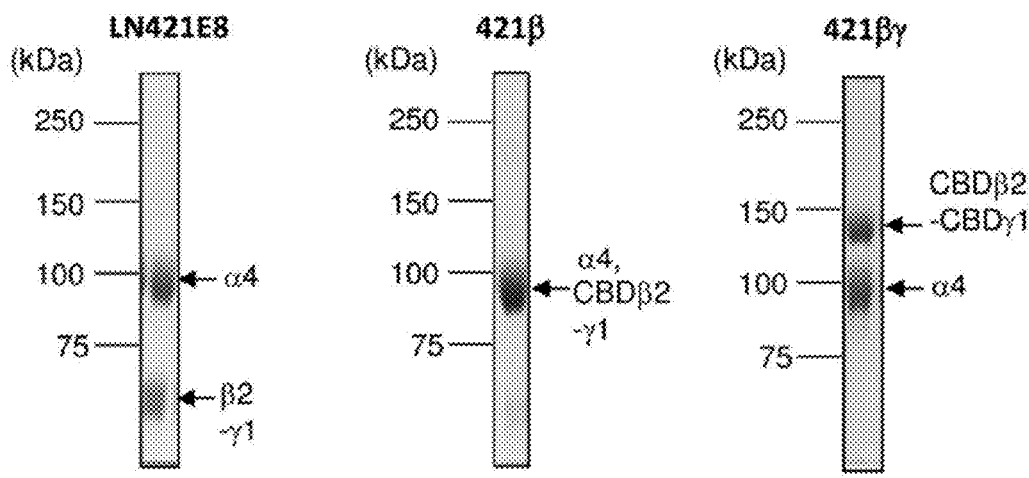
FIG. 13 shows the results of non-reducing SDS-PAGE analysis of a collagen binding domain (CBD)-free laminin 421E8 fragment and laminin 421E8 fragments fused with one or two CBDs.
Figure 12:
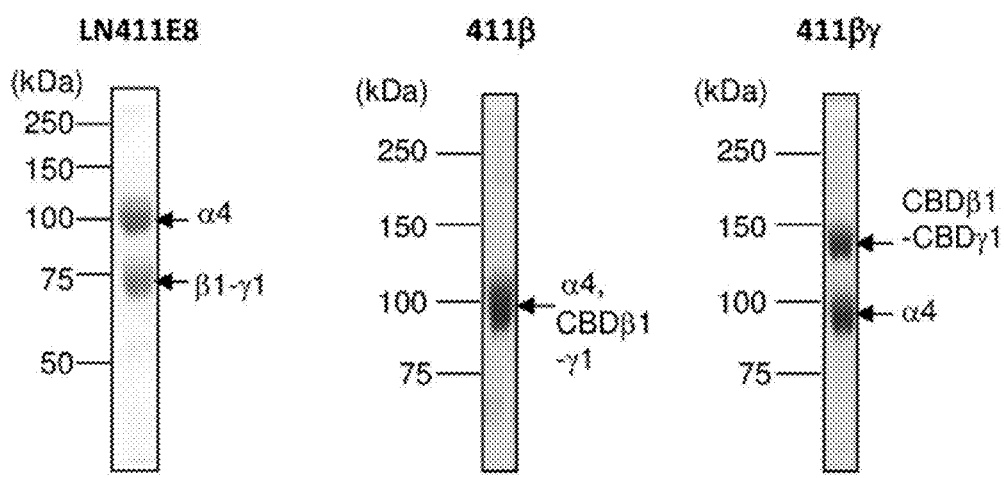
Figure 13:
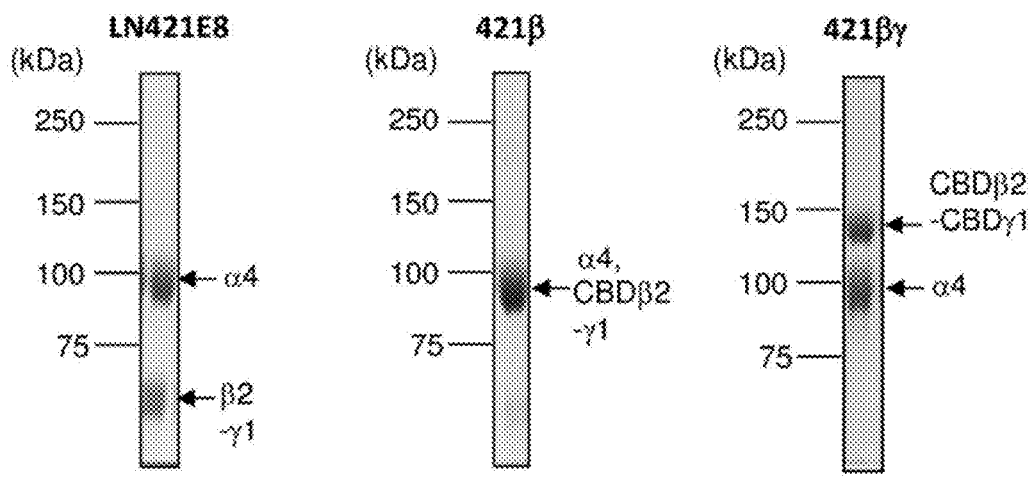
Figure 14:
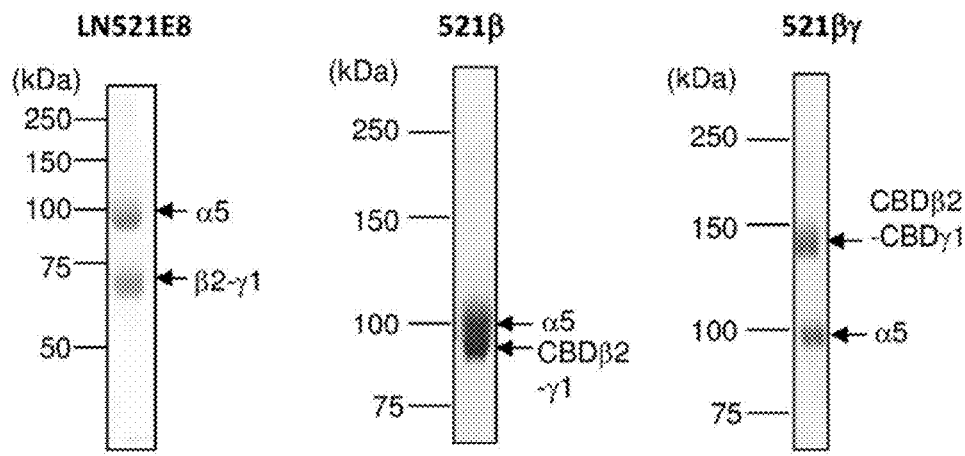
FIG. 14 shows the results of non-reducing SDS-PAGE analysis of a collagen binding domain (CBD)-free laminin 521E8 fragment and laminin 521E8 fragments fused with one or two CBDs.
Figure 15:
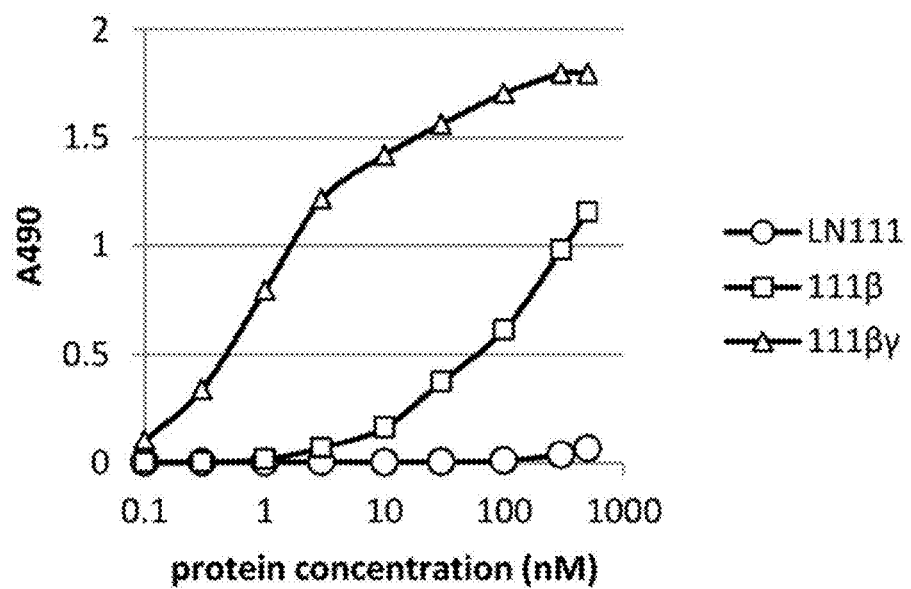
FIG. 15 shows the results on collagen binding activities of the collagen binding domain (CBD)-free laminin 111E8 fragment and the laminin 111E8 fragments fused with one or two CBDs.
Figure 16:
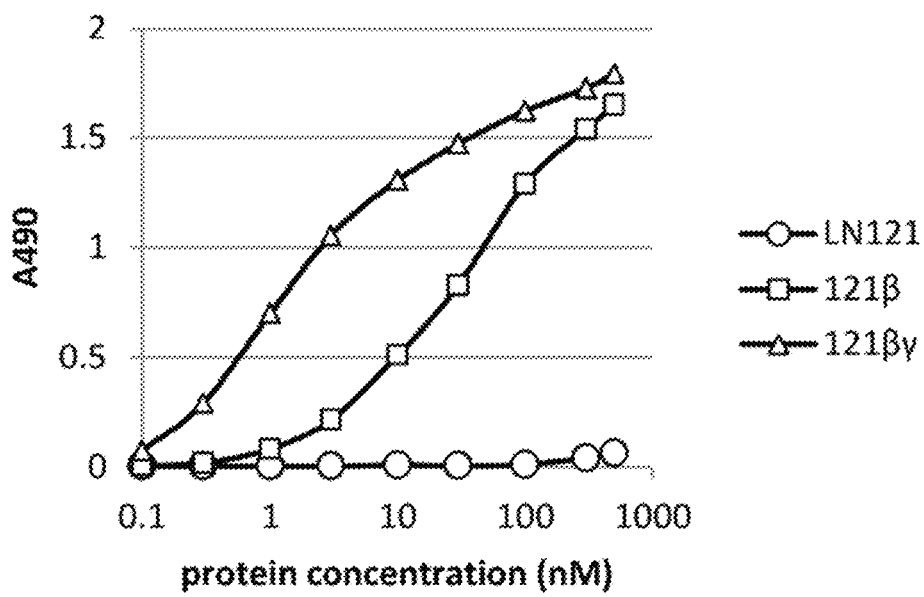
FIG. 16 shows the results on collagen binding activities of the collagen binding domain (CBD)-free laminin 121E8 fragment and the laminin 121E8 fragments fused with one or two CBDs.
Figure 17:
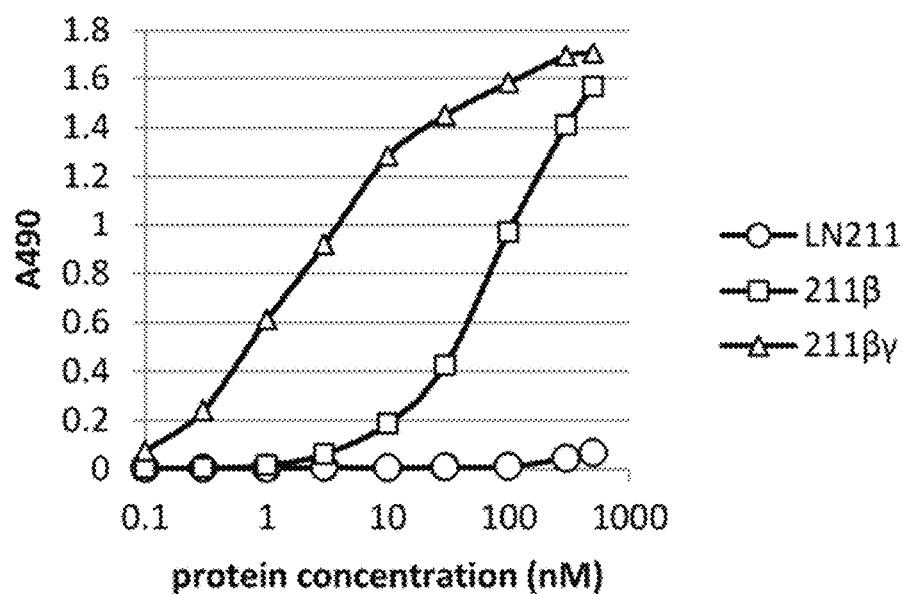
FIG. 17 shows the results on collagen binding activities of the collagen binding domain (CBD)-free laminin 211E8 fragment and the laminin 211E8 fragments fused with one or two CBDs.
Figure 18:
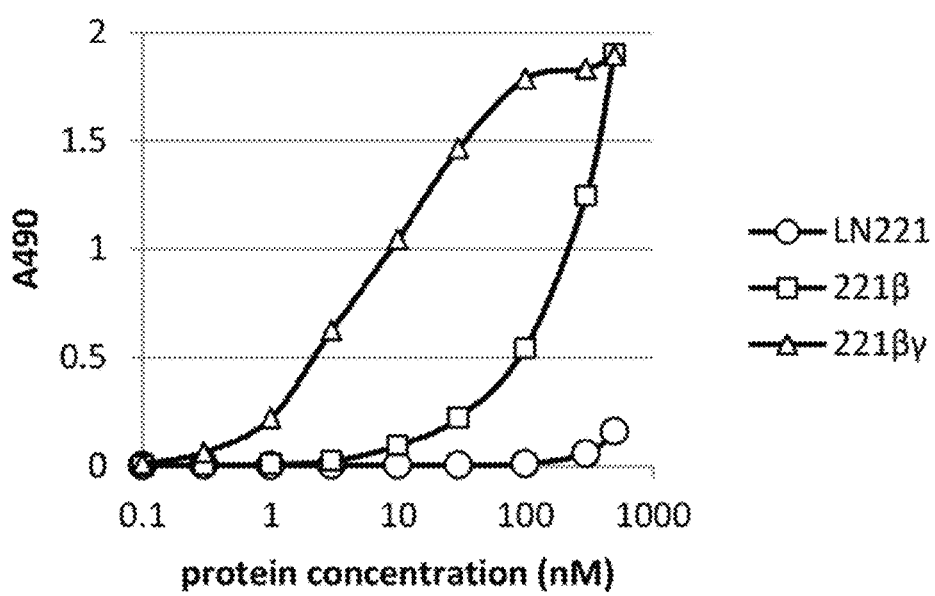
FIG. 18 shows the results on collagen binding activities of the collagen binding domain (CBD)-free laminin 221E8 fragment and the laminin 221E8 fragments fused with one or two CBDs.
Figure 19:
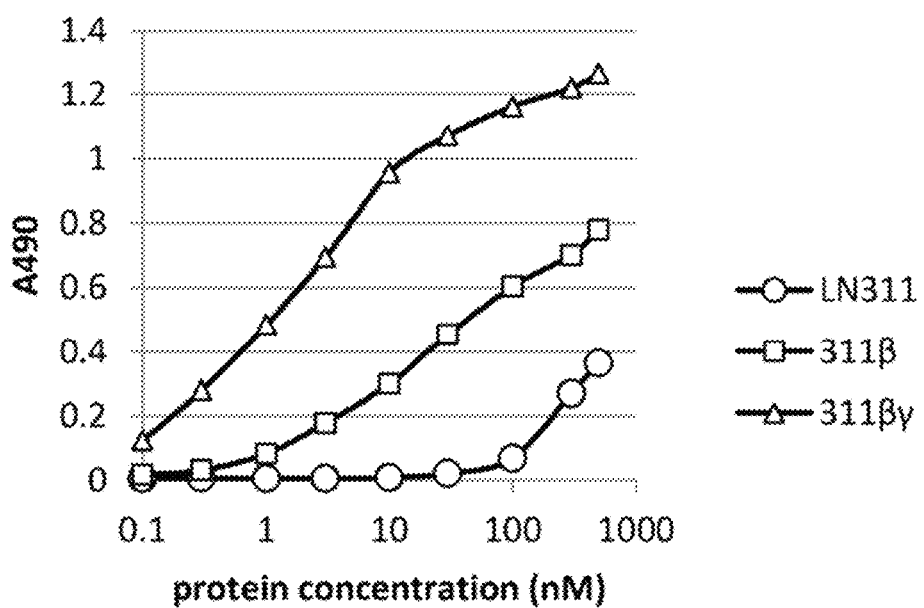
FIG. 19 shows the results on collagen binding activities of the collagen binding domain (CBD)-free laminin 311E8 fragment and the laminin 311E8 fragments fused with one or two CBDs.
Figure 20:
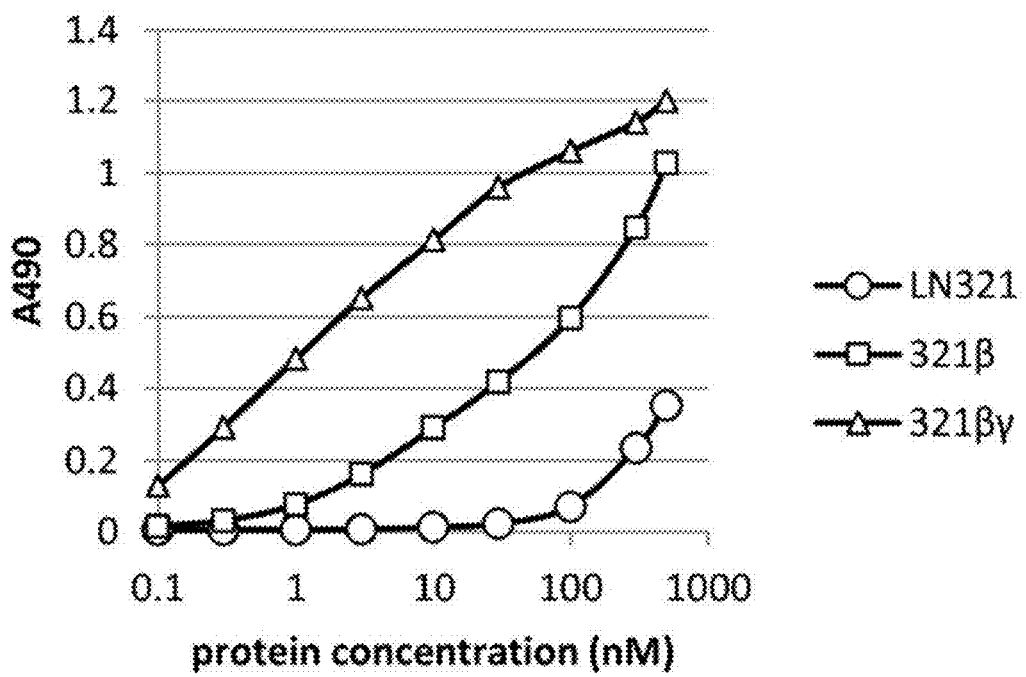
FIG. 20 shows the results on collagen binding activities of the collagen binding domain (CBD)-free laminin 321E8 fragment and the laminin 321E8 fragments fused with one or two CBDs.
Figure 21:
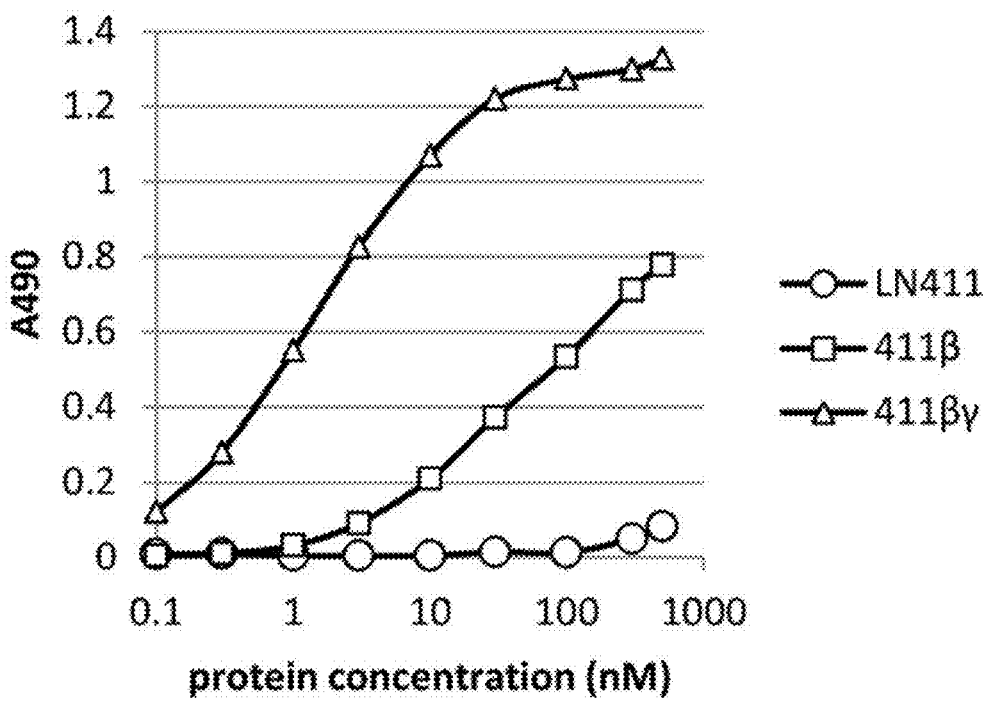
FIG. 21 shows the results on collagen binding activities of the collagen binding domain (CBD)-free laminin 411E8 fragment and the laminin 411E8 fragments fused with one or two CBDs.
Figure 22:
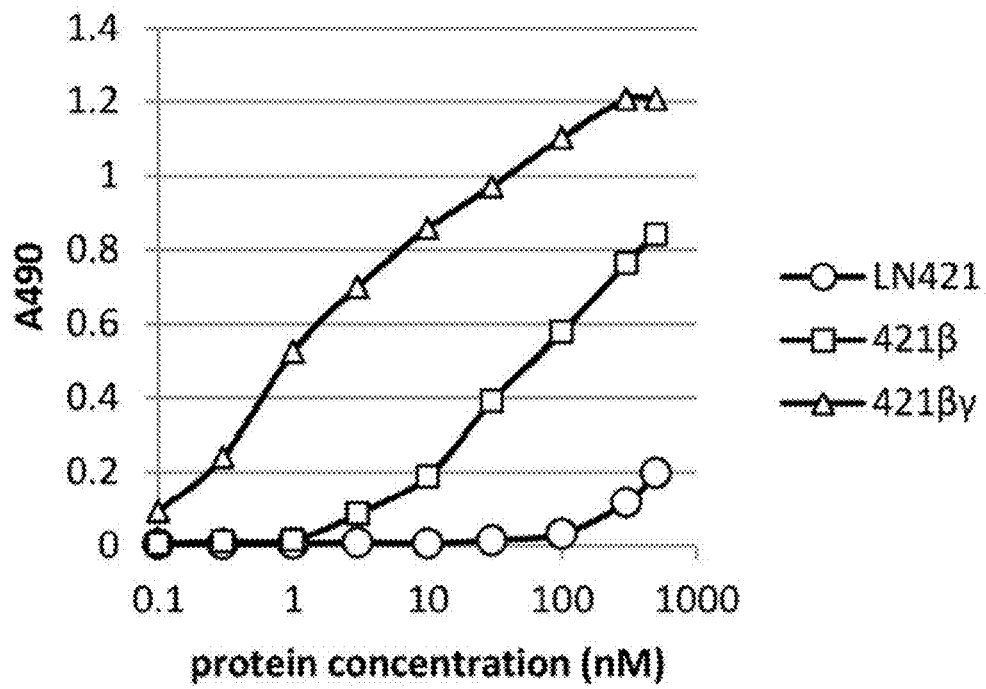
FIG. 22 shows the results on collagen binding activities of the collagen binding domain (CBD)-free laminin 421E8 fragment and the laminin 421E8 fragments fused with one or two CBDs.
Figure 23:
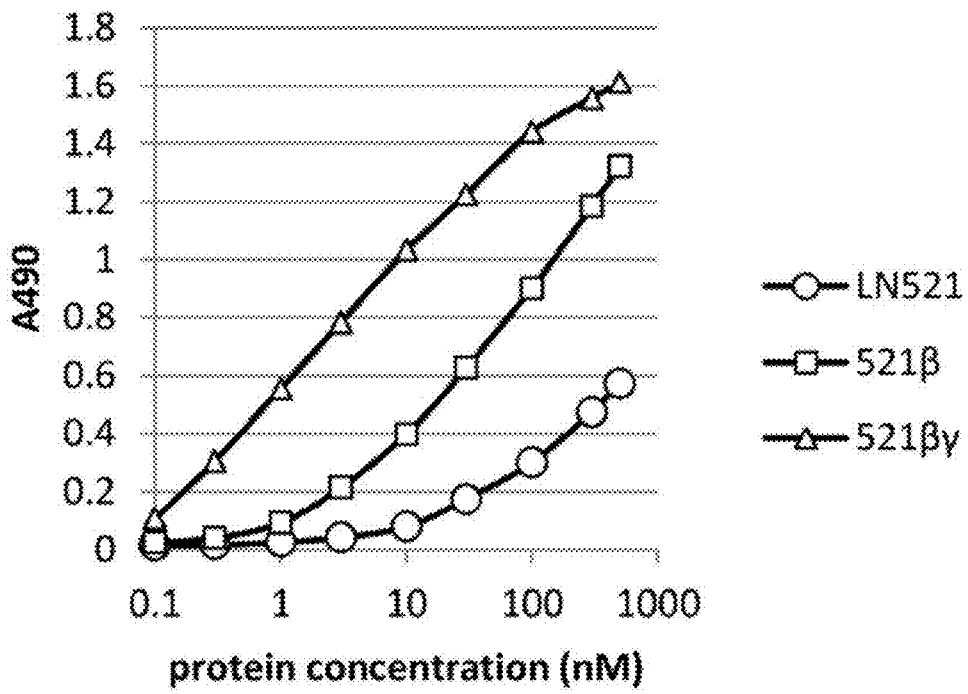
FIG. 23 shows the results on collagen binding activities of the collagen binding domain (CBD)-free laminin 521E8 fragment and the laminin 521E8 fragments fused with one or two CBDs.

The images of the iPS cells on day 3 of culture under gelatin-coating conditions are shown in FIG. 5. As is clear from FIG. 5, the gelatin-coating conditions produced more remarkable differences in the proliferation of iPS cells than the type I collagen-coating conditions. The iPS cells only slightly proliferated on the plate coated only with gelatin (indicated as "Gelatin only" in the figure), and the same was the case on the plate coated additionally with the CBD-free LN511-E8 (indicated as "+51E8" in the figure). When the plates were coated additionally with the LN511-E8 fused with a single CBD (indicated as "+CBD-E8 (β)" and "+CBD-E8 (γ)" in the figure), proliferation of the iPS cells was observed. On the plate coated additionally with the LN511-E8 fused with two CBDs (indicated as "+CBD-E8 (βγ)" in the figure), the number of iPS cells was greater than those observed on the plates coated additionally with the LN511-E8 fused with a single CBD.

Example 4: Preparation of Recombinant CBD-Fused Laminin E8 Fragments Derived from Laminin Isoforms Other than Laminin 511

In addition to the expression vectors for the E8 fragments of the chains prepared in Example 1, expression vectors for the E8 fragments of human laminin α chains other than the α5 chain (α1 chain E8, α2 chain E8, α3 chain E8 and α4 chain E8), an expression vector for laminin β2 chain E8, and an expression vector for CBD-fused laminin β2 chain E8 were separately prepared. Regarding the γ chain, the expression vector for laminin γ1 chain E8 and the expression vector for CBD-fused laminin γ1 chain E8 prepared in Example 1 were used. These vectors were co-transfected in a given combination into host cells for preparation of recombinant laminin E8 fragments and recombinant CBD-f used laminin E8 fragments derived from laminin isoforms other than laminin 511.
(1) Construction of Expression Vectors
(1-1) Preparation of Expression Vector for Human Laminin α1 Chain E8 Fragment PCR was performed using a cloning plasmid pBluescript KS(+) (Stratagene) as a template to prepare a pBluescript KS(+) containing a restriction enzyme AscI recognition sequence and a 6×His tag-encoding DNA at the 5' end of the EcoRV site in the multicloning site. The set of primers used for the PCR is the following (i).
(i) Primers for Insertion of 6×His Tag and AscI Site

```
                                   (forward, SEQ ID NO: 7)
    5'-ATGATGATGGGCGCGCCAAGCTTATCGATACCGT-3'

(reverse, SEQ ID NO: 8)
    5'-CATCATCATGATATCGAATTCCTGC-3'
```

Next, PCR was performed using a plasmid containing the cDNA sequence of the human laminin α1 chain (Ido et al., J. Biol. Chem., 279, 10946-10954, 2004) as a template to amplify a region corresponding to the α1 chain (accession number: NP_005550 (see Table 2), Phe1878 to Gln2700). The reverse primer contained a BamHI recognition sequence in the 5'-terminal region.

The amplified cDNA was inserted into the EcoRV-BamHI site in the multicloning site of the above-prepared pBluescript KS(+) containing an AscI recognition sequence and a 6×His tag-encoding sequence. From the resulting plasmid, a cDNA encompassing the α1 chain E8 fragment-encoding sequence and the 5'-terminal 6×His tag-encoding sequence was cut out with restriction enzymes AscI and BamHI, and inserted into the corresponding restriction site of a mammalian cell expression vector pSecTag2A (Invitrogen) to give an expression vector for the human α1 chain E8 fragment (containing a 6×His tag in the N-terminal region), which was named pSec-LNα1E8.
(1-2) Preparation of Expression Vector for Human Laminin α2 Chain E8 Fragment PCR was performed using a plasmid containing the cDNA sequence of the human laminin α2 chain (Ido et al., J. Biol. Chem., 283, 28149-28157, 2008) as a template to amplify a region corresponding to the α2 chain (accession number: NP_000417 (see Table 2), Leu1900 to Ala2722). The reverse primer contained a BamHI recognition sequence (GGATCC) in the 5'-terminal region.

The amplified cDNA was inserted into the EcoRV-BamHI site in the multicloning site of the above-prepared pBluescript KS(+) containing an AscI recognition sequence and a 6×His tag-encoding sequence. From the resulting plasmid, a cDNA encompassing the α1 chain E8 fragment-encoding sequence and the 5'-terminal 6×His tag-encoding sequence was cut out with restriction enzymes AscI and BamHI, and inserted into the corresponding restriction site of a mammalian cell expression vector pSecTag2A (Invitrogen) to give an expression vector for the human α2 chain E8 fragment (containing a 6×His tag in the N-terminal region), which was named pSec-LNα2E8.
(1-3) Preparation of Expression Vector for Human Laminin α3 Chain E8 Fragment PCR was performed using a plasmid containing the cDNA sequence of the human laminin α3 chain (lacking the 4th and 5th laminin globular domains) (Ido et al., J. Biol. Chem., 282, 11144-11154, 2007) as a template to amplify a region corresponding to the α3 chain (accession number: NP_000218 (see Table 2), Ala579 to Ala1364). The reverse primer contained a XbaI recognition sequence in the 5'-terminal region.

The amplified cDNA was inserted into the EcoRV-XbaI site in the multicloning site of the above-prepared pBluescript KS(+) containing an AscI recognition sequence and a 6×His tag-encoding sequence. From the resulting plasmid, a cDNA encompassing the α3 chain E8 fragment-encoding sequence and the 5'-terminal 6×His tag-encoding sequence was cut out with restriction enzymes AscI and NotI, and inserted into the corresponding restriction site of a mammalian cell expression vector pSecTag2A (Invitrogen) to give an expression vector for the human α3 chain E8 fragment (containing a 6×His tag in the N-terminal region), which was named pSec-LNα3E8.
(1-4) Preparation of Expression Vector for Human Laminin α4 Chain E8 Fragment For preparation of a cDNA fragment encoding a mouse Ig-κ chain V-J2-C signal peptide, a 6×His tag and an α4 chain E8 fragment in this order from the 5' end, a cDNA fragment encoding the mouse Ig-κ chain V-J2-C signal peptide and the 6×His tag, and a cDNA fragment encoding the α4 chain E8 were separately obtained, and these two fragments were joined and amplified by extension PCR.

First, PCR was performed using an expression vector for human laminin α5 chain E8 (Ido et al., J. Biol. Chem., 282, 11144-11154, 2007) as a template to amplify a region corresponding to the mouse Ig-κ chain V-J2-C signal peptide and the 6×His tag. The set of primers used for the PCR is the below (ii). The reverse primer contained a sequence used for extension PCR in the 5'-terminal region.
(ii) Primers for Amplification of Signal Peptide Sequence and 6×His Tag Sequence

```
                                    (forward, SEQ ID NO: 9)
    5'-GAGGTCTATATAAGCAGAGCTCTCTGGCTAACTA-3'

(reverse, SEQ ID NO: 10)
    5'-CATTGGCTTCATCATGATGATGATGATGATGAAGC-3'
```

Next, PCR was performed using a plasmid containing the cDNA sequence of the human laminin α4 chain (Hayashi et al., Biochem Biophys Res Commun., 299, 498-504, 2002) as a template to amplify a region corresponding to the α4 chain (accession number: NP_002281 (see Table 2), Glu629 to His1449). The forward primer contained a sequence used for extension PCR in the 5'-terminal region, and the reverse primer contained an EcoRI recognition sequence in the 5'-terminal region.

The obtained two kinds of cDNA fragments were joined and amplified by extension PCR to give a cDNA fragment encoding the mouse Ig-κ chain V-J2-C signal peptide, the 6×His tag and the α4 chain E8. The amplified cDNA was digested with restriction enzymes HindIII and EcoRI. The digested fragment was inserted into the corresponding restriction site of a mammalian cell expression vector pSecTag2B (invitrogen) to give an expression vector for the human α4 chain E8 fragment (containing a 6×His tag in the N-terminal region), which was named pSec-LNα4E8.

(1-5) Preparation of Expression Vector for Human Laminin β2 Chain E8 Fragment

PCR was performed using a plasmid containing the cDNA sequence of the human laminin β2 chain (Ido et al., J. Biol. Chem., 283, 28149-28157, 2008) as a template to amplify a region corresponding to human laminin β2E8 (accession number: NP_002283 (see Table 2), Leu1573-Gln1798). The reverse primer contained an EcoRI recognition sequence in the 5'-terminal region. A fragment containing a cDNA and an HA tag-encoding DNA fused to the 5' end of the cDNA was amplified by PCR.

The amplified cDNA was inserted into the EcoRV-EcoRI site in the multicloning site of a pBluescript KS(+) containing an HA tag-encoding sequence. From the resulting plasmid, a cDNA encompassing the β2 chain E8 fragment-encoding sequence and the 5'-terminal HA tag-encoding sequence was cut out with restriction enzymes KpnI and EcoRI, and inserted into the corresponding restriction site of a mammalian cell expression vector pSecTag2B (Invitrogen) to give an expression vector for the human β2 chain E8 fragment (containing an HA tag in the N-terminal region), which was named pSec-LNβ2E8 (Taniguchi Y. et al., J. Biol. Chem. 2009, 284-7820-7831).

(1-6) Preparation of Expression Vector for CBD-Fused Human Laminin 32 Chain E8 Fragment A cDNA encoding CBD (accession number: NP_997647 (see Table 3), Val276-Thr604) was amplified by PCR to give a product with a 5'-end HindIII site. A fragment composed of a human laminin β2E8-encoding cDNA and an HA tag-encoding DNA fused to the 5' end of the cDNA was amplified by PCR, and then fused to the CBD-encoding DNA fragment by PCR. The resulting fragment was inserted into the HindIII/EcoRI site of a pSecTag2B vector (Invitrogen) to give pSec-CBD-LNβ2E3.

The amino acid sequence of a protein expressed by the pSec-CBD-LNβ2E8 (CBD-LNβ2E8) is shown in SEQ ID NO: 11, and the nucleotide sequence of the corresponding DNA (contained in the Sec-CBD-LNβ2E8) is shown in SEQ ID NO: 12.

(2) Expression and Purification of Recombinant Laminin E8 Fragments and Recombinant CBD-Fused Laminin E8 Fragments Recombinant laminin E8 fragments and recombinant CBD-fused laminin E8 fragments were prepared using the FreeStyle™ 293 Expression System (Invitrogen) according to the procedure described in Example 1. For purification of each recombinant protein secreted in the culture medium, the conditioned medium was subjected to two-step affinity chromatography using Ni-NTA agarose and anti-FLAG M2 agarose according to the procedure described in Example 1. Each purified recombinant protein was dialyzed against PBS, the dialyzed product was sterilized by filtration through a 22-μm disk syringe filter (Millipore, #SLGV033RS) and the filtrate was stored at −80° C. The combinations of the expression vectors used for the preparation of the recombinant CBD-fused laminin E8 fragments and the recombinant laminin E8 fragments are shown in Table 5.

TABLE 5

| | α chain E8 expression vector | β chain E8 expression vector | γ chain E8 expression vector |
|---|---|---|---|
| LN111-E8 | LNα1E8 | LNβ1E8 | LNγ1E8 |
| 111β | LNα1E8 | CBD-LNβ1E8 | LNγ1E8 |
| 111βγ | LNα1E8 | CBD-LNβ1E8 | CBD-LNγ1E8 |
| LN121E8 | LNα1E8 | LNβ2E8 | LNγ1E8 |
| 121β | LNα1E8 | CBD-LNβ2E8 | LNγ1E8 |
| 121βγ | LNα1E8 | CBD-LNβ2E8 | CBD-LNγ1E8 |
| LN211E8 | LNα2E8 | LNβ1E8 | LNγ1E8 |
| 211β | LNα2E8 | CBD-LNβ1E8 | LNγ1E8 |
| 211βγ | LNα2E8 | CBD-LNβ1E8 | CBD-LNγ1E8 |
| LN221E8 | LNα2E8 | LNβ2E8 | LNγ1E8 |
| 221β | LNα2E8 | CBD-LNβ2E8 | LNγ1E8 |
| 221βγ | LNα2E8 | CBD-LNβ2E8 | CBD-LNγ1E8 |
| LN311E8 | LNα3E8 | LNβ1E8 | LNγ2E8 |
| 311β | LNα3E8 | CBD-LNβ1E8 | LNγ1E8 |
| 311βγ | LNα3E8 | CBD-LNβ1E8 | CBD-LNγ1E8 |
| LN321E8 | LNα3E8 | LNβ2E8 | LNγ1E8 |
| 321β | LNα3E8 | CBD-LNβ2E8 | LNγ1E8 |
| 321βγ | LNα3E8 | CBD-LNβ2E8 | CBD-LNγ1E8 |
| LN411E8 | LNα4E8 | LNβ1E8 | LNγ1E8 |
| 411β | LNα4E8 | CBD-LNβ1E8 | LNγ1E8 |
| 411βγ | LNα4E8 | CBD-LNβ1E8 | CBD-LNγ1E8 |
| LN421E8 | LNα4E8 | LNβ2E8 | LNγ1E8 |
| 421β | LNα4E8 | CBD-LNβ2E8 | LNγ1E8 |
| 421βγ | LNα4E8 | CBD-LNβ2E8 | CBD-LNγ1E8 |
| LN521E8 | LNα5E8 | Lnβ2E8 | LNγ1E8 |
| 521β | LNα5E8 | CBD-LNβ2E8 | LNγ1E8 |
| 521βγ | LNα5E8 | CBD-LNβ2E8 | CBD-LNγ1E8 |

(3) SDS-PAGE Analysis of Recombinant Laminin E8 Fragments and Recombinant CBD-Fused Laminin E8 Fragments The concentrations of the purified proteins were determined by the BCA assay using bovine serum albumin (BSA) as a standard. The purities of the purified proteins were determined by non-reducing SDS-PAGE and subsequent Coomassie Brilliant Blue staining.

The results of the SDS-PAGE of the recombinant laminin. E8 fragments and the recombinant CBD-fused laminin E8 fragments derived from various isoforms are shown in FIGS. 6 to 14. In each sample, two bands corresponding to a monomer of α chain E8 and a dimer of β chain E8 and γ1 chain E8 were detected under non-reducing conditions, revealing that the recombinant laminin E8 fragments and the recombinant CBD-fused laminin E8 fragments were successfully purified as heterotrimeric proteins, as is the case with the laminin 511E8 fragment and the CBD-fused laminin 511E8 fragments.

Example 5: Examination on Collagen Binding Activities of Recombinant CBD-Fused Laminin E8 Fragments Derived from Laminin Isoforms Other than Laminin 511

(1) Binding Activity Measurement

Collagen binding activities were measured in the same manner as in Example 2 (1) except that "an anti-FLAG antibody M2 (Sigma) diluted 2000-fold in a wash buffer" was used instead of "the anti-laminin α5 antibody 5D6-containing antiserum diluted 3000-fold in a wash buffer."

The results on type I collagen binding activities are shown in FIGS. 15 to 23. The CBD-free laminin E8 fragments (indicated as LN111E8, LN121E8, LN211E8, LN221E8, LN311E8, LN321E8, LN411E8, LN421E8 and LN521E8 in the figures) hardly bound to type I collagen, but 111β, 121β, 211β, 221β, 311β, 321β, 411β, 421β and 521β, which contained a single CBD fused to the β chain, were remarkably capable of binding to type I collagen. In addition, 111βγ, 121βγ, 211βγ, 221βγ, 311βγ, 321βγ, 411βγ, 421βγ and 521βγ, which contained CBDs fused to both the β and γ1 chains, bound to type I collagen at lower concentrations as compared with the corresponding single CBD-fused E8 fragments. These results showed that the type I collagen binding activities of the forms with two CBDs (divalent forms) were higher by 10-fold or more than those of the forms with a single CBD (monovalent forms).

The present invention is not limited to the particular embodiments and examples described above, and various modifications can be made within the scope of the appended claims. Other embodiments provided by suitably combining technical means disclosed in separate embodiments of the present invention are also within the technical scope of the present invention. All the academic publications and patent literature cited in the description are incorporated herein by reference.

The invention claimed is:

1. A modified laminin wherein at least one of the α chain N-terminus, the β chain N-terminus and the γ chain N-terminus of a heterotrimeric laminin E8 fragment is fused with a collagen binding molecule, wherein the heterotrimeric laminin E8 fragment has integrin binding activity, and wherein the collagen binding molecule is selected from the group consisting of:

(a) fibronectin or a fragment having a collagen binding domain thereof, (b) collagenase or a fragment having a collagen binding domain thereof, (c) integrin α1 chain or a fragment having a collagen binding domain thereof, (d) integrin α2 chain or a fragment having a collagen binding domain thereof, (e) integrin α10 chain or a fragment having a collagen binding domain thereof, (f) integrin α11 chain or a fragment having a collagen binding domain thereof, (g) platelet glycoprotein VI or a fragment having a collagen binding domain thereof,
(h) discoidin domain receptor 1 or a fragment having a collagen binding domain thereof,
(i) discoidin domain receptor 2 or a fragment having a collagen binding domain thereof,
(l) mannose receptor or a fragment having a collagen binding domain thereof,
(k) phospholipase A2 receptor or a fragment having a collagen binding domain thereof,
(l) DEC205 or a fragment having a collagen binding domain thereof,
(m) Endo180 or a fragment having a collagen binding domain thereof,
(n) von Willebrand factor or a fragment having a collagen binding domain thereof,
(o) MMP-2 or a fragment having a collagen binding domain thereof,
(p) MMP-9 or a fragment having a collagen binding domain thereof,
(q) leukocyte-associated immunoglobulin-like receptor 1 or a fragment having a collagen binding domain thereof, and
(r) leukocyte-associated immunoglobulin-like receptor 2 or a fragment having a collagen binding domain thereof.

2. The modified laminin according to claim 1, wherein the heterotrimeric laminin E8 fragment has the collagen binding molecules conjugated to two or more sites selected from the α chain N-terminus, the β chain N-terminus and the γ chain N-terminus.

3. The modified laminin according to claim 1, wherein the heterotrimeric laminin E8 fragment consists of one kind of E8 fragment of α chain selected from α1 to α5, one kind of E8 fragment of β chain selected from β1 to β3, and one kind of E8 fragment of γ chain selected from γ1 to γ3.

4. The modified laminin according to claim 3, wherein the heterotrimeric laminin E8 fragment is laminin α5β1γ1 E8 fragment, laminin α3β3γ2 E8 fragment, laminin α1β1γ1 E8 fragment, laminin α1β2γ1 E8 fragment, laminin α2β1γ1 E8 fragment, laminin α2β2γ1 E8 fragment, laminin α3β1γ1 E8 fragment, laminin α3β2γ1 E8 fragment, laminin α4β1γ1 E8 fragment, laminin α4β2γ1 E8 fragment, or laminin α5β2γ1 E8 fragment.

5. An extracellular-matrix material comprising the modified laminin according to claim 1, and collagen and/or gelatin.

6. A culture substrate coated with the modified laminin according to claim 1, and collagen and/or gelatin.

7. A scaffold comprising the modified laminin according to claim 1, and collagen and/or gelatin.

8. A method for culturing mammalian cells comprising culturing the cells in the presence of the modified laminin according to claim 1, and collagen and/or gelatin.

9. The method according to claim 8, wherein the mammalian cells are embryonic stem (ES) cells, induced pluripotent stem (iPS) cells or somatic stem cells.

* * * * *